US011164669B1

(12) United States Patent
Neumann

(10) Patent No.: US 11,164,669 B1
(45) Date of Patent: Nov. 2, 2021

(54) SYSTEMS AND METHODS FOR GENERATING A VIRAL ALLEVIATION PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/136,102

(22) Filed: Dec. 29, 2020

(51) Int. Cl.
*G16H 20/60* (2018.01)
*G16H 10/60* (2018.01)
(Continued)

(52) U.S. Cl.
CPC ............. *G16H 20/60* (2018.01); *G06N 3/08* (2013.01); *G16H 10/40* (2018.01); *G16H 10/60* (2018.01);
(Continued)

(58) Field of Classification Search
CPC ........ G16H 20/60; G16H 10/40; G16H 70/60; G16H 50/80; G16H 50/20; G16H 50/70; G16H 10/60; G06N 3/08
See application file for complete search history.

(56) References Cited

U.S. PATENT DOCUMENTS

| | | |
|---|---|---|
| 2016/0091419 A1 | 3/2016 | Watson |
| 2016/0306931 A1 | 10/2016 | Lahteenmaki |

(Continued)

FOREIGN PATENT DOCUMENTS

| | | |
|---|---|---|
| CN | 109545328 | 3/2019 |
| IN | 202041024942 | 6/2020 |

(Continued)

OTHER PUBLICATIONS

Agrebi S, Larbi A. Use of artificial intelligence in infectious diseases. Artificial Intelligence in Precision Health. 2020:415-38. doi: 10.1016/B978-0-12-817133-2.00018-5. Epub Mar. 13, 2020. PMCID: PMC7153335. (Year: 2020).*

(Continued)

*Primary Examiner* — Evangeline Barr
(74) *Attorney, Agent, or Firm* — Caldwell Intellectual Property Law

(57) ABSTRACT

A system for generating a viral alleviation program including a computing device configured to receive at least a viral biomarker relating to a user, retrieve a viral epidemiological profile, identify, using the viral epidemiological profile, a plurality of nutrition elements for the user, wherein identifying includes assigning the viral epidemiological profile to a viral infection category, calculating, according to the viral infection category, a plurality of nutrient amounts, wherein calculating a plurality of nutrient amounts includes determining an effect of the plurality of nutrient amounts on the viral epidemiological profile, and calculating the plurality of nutrient amounts as a function of the effect, identifying, as a function of the plurality of nutrient amounts, the plurality of nutrition elements, wherein the plurality of nutrition elements are intended to prevent viral infection as a function of the viral infection category, and generate, using the plurality of nutrition elements, viral alleviation program.

18 Claims, 8 Drawing Sheets

(51) Int. Cl.
*G16H 70/60* (2018.01)
*G16H 50/70* (2018.01)
*G16H 50/20* (2018.01)
*G16H 50/80* (2018.01)
*G06N 3/08* (2006.01)
*G16H 10/40* (2018.01)
*A61B 5/00* (2006.01)
*G06N 3/04* (2006.01)

(52) U.S. Cl.
CPC ............ *G16H 50/20* (2018.01); *G16H 50/70* (2018.01); *G16H 50/80* (2018.01); *G16H 70/60* (2018.01); *A61B 5/4833* (2013.01); *G06N 3/04* (2013.01)

(56) References Cited

U.S. PATENT DOCUMENTS

| | | | |
|---|---|---|---|
| 2017/0249445 A1 | 8/2017 | Devries | |
| 2018/0286516 A1* | 10/2018 | Menichetti | G16H 50/70 |
| 2019/0172587 A1* | 6/2019 | Park | G06F 17/18 |
| 2019/0221303 A1* | 7/2019 | Bennett | G16H 50/30 |
| 2019/0251861 A1* | 8/2019 | Wolf | G16H 20/60 |
| 2019/0290172 A1 | 9/2019 | Hadad | |
| 2019/0341145 A1 | 11/2019 | Prakash | |
| 2020/0066181 A1 | 2/2020 | Hadjigeorgiou | |
| 2020/0185100 A1 | 6/2020 | Francois | |
| 2020/0312455 A1 | 10/2020 | Bhalotia | |
| 2020/0342545 A1 | 10/2020 | Dobson | |
| 2021/0050116 A1* | 2/2021 | Sabeti | G06Q 50/01 |

FOREIGN PATENT DOCUMENTS

| | | |
|---|---|---|
| IN | 202041031475 | 7/2020 |
| WO | 2020069500 | 4/2020 |
| WO | 2020239745 | 12/2020 |

OTHER PUBLICATIONS https://theana.org/COVID-19; Title: Personalized Nutrition & the COVID-19 Era; By: Victoria Yunez Behm; Date: Oct. 1, 2020.

https://www.frontiersin.org/articles/10.3389/fnut.2016.00005/full; Title: Modeling-Enabled Systems Nutritional Immunology; By: Meghna Verma; Date: Feb. 16, 2016.

Title: General Nutrition Management in Patients infected with Human Immunodeficiency Virus; By: Nerad; Date: 2003.

* cited by examiner

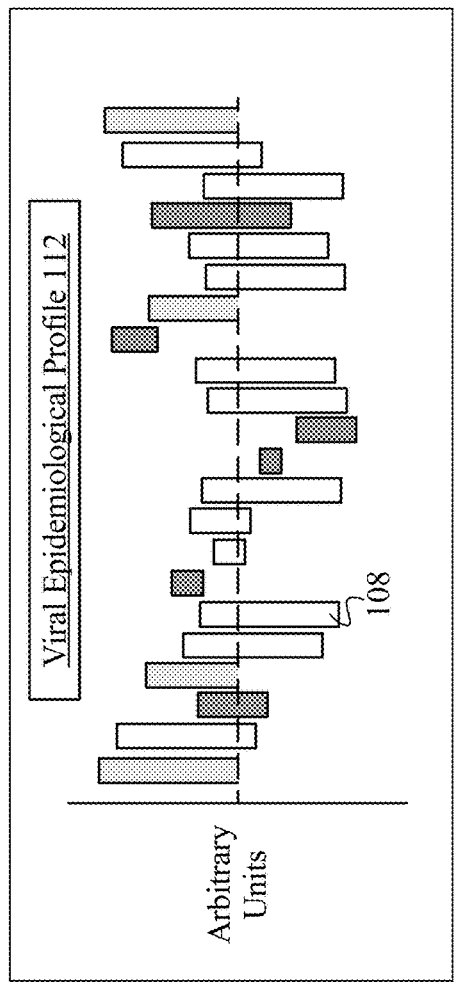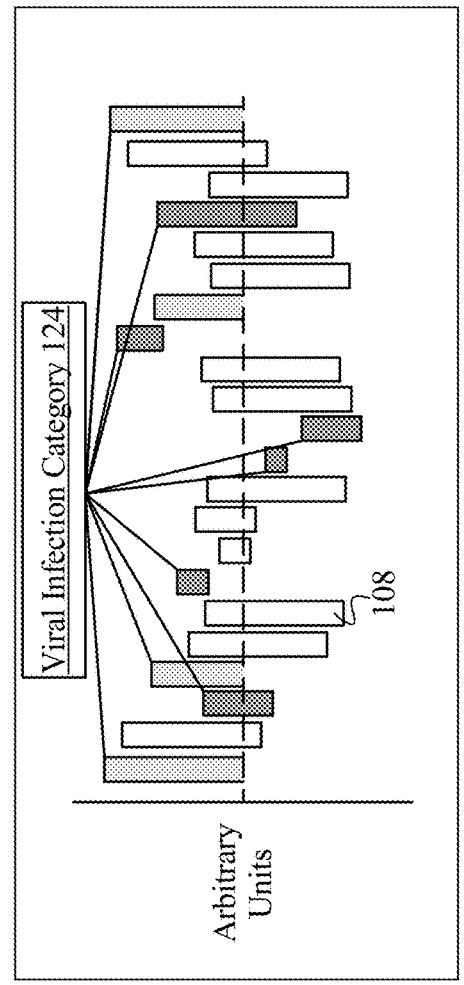

SYSTEMS AND METHODS FOR GENERATING A VIRAL ALLEVIATION PROGRAM

FIELD OF THE INVENTION

The present invention generally relates to the field of nutrition modeling for viral infection alleviation. In particular, the present invention is directed to generating a viral alleviation program.

BACKGROUND

It has been estimated that a large degree of viral infections may be preventable using a variety of strategies such as, masks, distancing, and handwashing. Although, priming the immunological response by pharmacological intervention, such as by vaccination, maintains the standard for prevention of viral infection.

SUMMARY OF THE DISCLOSURE

In an aspect, a system for generating a viral alleviation program including a computing device configured to receive at least a viral biomarker relating to a user, retrieve a viral epidemiological profile related to the user, identify, using the viral epidemiological profile, a plurality of nutrition elements for the user, wherein identifying includes assigning the viral epidemiological profile to a viral infection category, calculating, according to the viral infection category, a plurality of nutrient amounts, wherein calculating a plurality of nutrient amounts includes determining an effect of the plurality of nutrient amounts on the viral epidemiological profile, and calculating the plurality of nutrient amounts as a function of the effect, identifying, as a function of the plurality of nutrient amounts, the plurality of nutrition elements, wherein the plurality of nutrition elements are intended to prevent viral infection as a function of the viral infection category, and generate, using the plurality of nutrition elements, viral alleviation program.

In another aspect, a method for generating a viral alleviation program including receiving, by a computing device, at least a viral biomarker relating to a user, retrieving, by the computing device, a viral epidemiological profile related to the user, identifying, by the computing device, using the viral epidemiological profile, a plurality of nutrition elements for the user, wherein identifying includes assigning the viral epidemiological profile to a viral infection category, calculating, according to the viral infection category, a plurality of nutrient amounts, wherein calculating a plurality of nutrient amounts includes determining an effect of the plurality of nutrient amounts on the viral epidemiological profile, and calculating the plurality of nutrient amounts as a function of the effect, identifying, as a function of the plurality of nutrient amounts, the plurality of nutrition elements, wherein the plurality of nutrition elements are intended to prevent viral infection as a function of the viral infection category, and generating, by the computing device, using the plurality of nutrition elements, viral alleviation program.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A and 4B are a diagrammatic representation of a viral epidemiological profile;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a viral alleviation program. In an embodiment, system includes a computing device configured to receive viral biomarkers of a user. Viral biomarkers may include experimental testing results, such as PCR test data, antigen testing, antibody testing, ELISA, etc. Computing device is configured to retrieve a viral epidemiological profile, which may include a variety of data used to generate a phylogenic profile of a virus. Computing device may generate viral epidemiological profile, by using a machine-learning algorithm to model viral incidence to a plurality of viral epidemiological factors, such as detection, transmission chain, and spread. Computing device is configured to determine the effect of nutrients on the user's viral epidemiological profile. Computing device may generate a spread model which models a plurality of effects of the plurality of nutrient amounts on viral spread rates, determining unique effects for a plurality of nutrients. Computing device may identify nutrition elements, such as individual ingredients, and calculate a viral alleviation program using the calculated nutrient amounts and their effects according to viral biomarkers. In an embodiment, computing device may accept user input and generate viral alleviation program, where elements are curated according to the user input. Participation and adherence to viral alleviation program may be used to provide a viral alleviation metric. Computing device may calculate changes in the incidence of viral infection in the user according to adherence to viral alleviation program.

Figure 1:
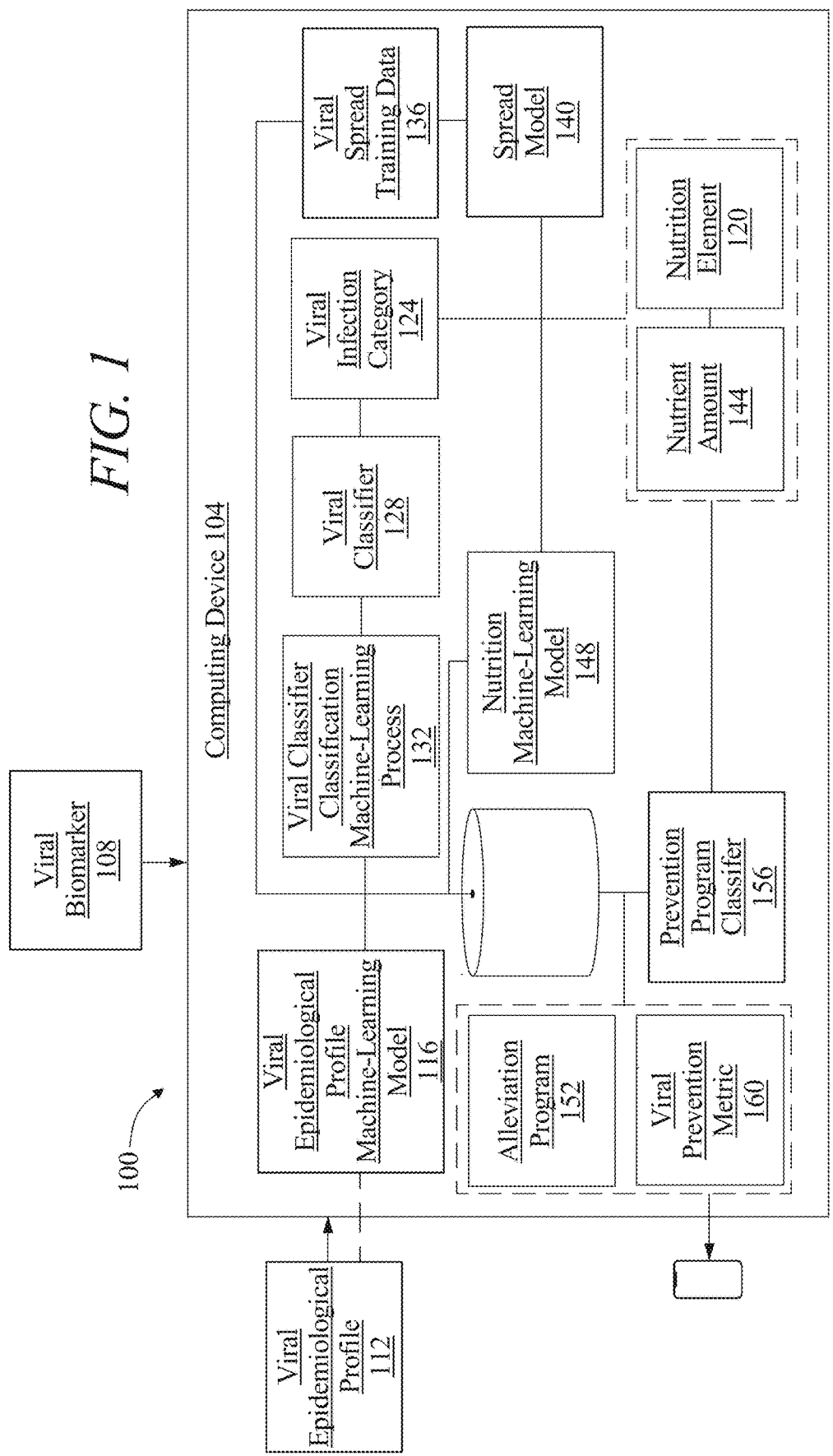
FIG. 1 is a block diagram illustrating a system for generating a viral alleviation program.

Referring now to FIG. 1, an exemplary embodiment of a system 100 for generating a viral alleviation program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a viral biomarker related to a user. A "viral biomarker," as used in this disclosure, is a biological and/or chemical substance or process that is indicative of the presence of viral infection in the body. Viral biomarker 108 may include biological molecules existing within a normal cell, an infected cell, secreted by a viral-infected cell, and/or a specific response of the body to the presence of viruses. Receiving at least the viral biomarker 108 may include receiving a result of one or more tests relating the user. Viral biomarker 108 may include test results of screening and/or early detection of viruses, for instance from a PCR test (qPCR, qtPCR, RTPCR etc.), viral antigen test, antibody test, enzyme-linked immunosorbent assay (ELISA), T-cell activation test, among other biochemical data. Test may include diagnostic procedures, prognostic indicators from other diagnoses, from predictors identified in a medical history, and information relating to biomolecules associated with viral infection such as: interleukin (IL) IL-1B, IL-1-RA, IL-2, IL-6, IL-8, IL-10, MIP-1alpha, MIP-1Beta, MCP-1, MCSF, MIF, IP-10, GRO-alpha, eotaxin, neopterin, sTNF-RI, TNF-alpha, sFasL, sFAS, IFN-alpha, IFN-gamma, CCL17, CXCL5, CXCL9, IP-10, CXCL11, mixed lineage kinase domain-like protein (MLKL), urea, creatinine, cystatin C, bilirubin, cholinesterase, procalcitonin, and the like. Persons skilled in the art may appreciate the full spectrum of biochemical data relating to the body that may be indicative of viral infection and/or may constitute a "viral biomarker," as described herein.

Continuing in reference to FIG. 1, test may include results enumerating the relationships between proteins, DNA, RNAs, white blood cells, among other macromolecules, signaling peptides, and the like, such as increases/decreases in concentrations of cytokines, ratios of cytokine concentrations, complement pathway proteins, phosphorylation states, presence of dsRNA, and the like. Test results may indicate the presents of genetic insertions, deletions, translocations, inversions, gene expression levels, single nucleotide polymorphisms (SNPs), etc., in genetic sequences that may make an individual more or less susceptible to a particular viral infection. For instance and without limitation, among Caucasians, a 32-base-pair deletion in the coding region of the chemokine receptor, CCR-5, which renders such individuals far more resistant to HIV-1 than those with intact alleles. Test results may indicate blood panel factors, microbiological factors, epigenetic factors, among other categories of biological, physiological, and chemical indicators of viral infection. Test may include a health state questionnaire, where a user may indicate a symptom relating to viral infection. Viral biomarker 108 may include hematological analysis including results from T-cell activation assays, abnormal nucleation of white blood cells, white blood cell counts, concentrations, recruitment, localization, and the like. Viral biomarker 108 may be received as a function of a user indicating a prior diagnosis, or a current medication, wherein one is a viral infection treatment, such as for treatment of Herpes, Hepatitis, HIV, Epstein-Barr virus, among other chronic and acute viral pathologies. Viral biomarker 108 may include any virus-related symptoms, side effects, and co-morbidities associated with and relating to viral infection diagnosis. Viral biomarker 108 may be received and/or identified from a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, viral biomarker 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, viral biomarker 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, viral biomarker 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Viral biomarker 108 training data may alternatively or additionally be implemented using a distributed data storage protocol and/or data structure, such as a distributed hash table and the like. Viral biomarker 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of viral biomarkers may be stored, retrieved, organized, and/or reflect data and/or records as used herein, as well as categories and/or populations of data consistent with this disclosure.

Continuing in reference to FIG. 1, computing device is configured to retrieve a viral epidemiological profile related to the user. A "viral epidemiological profile," as used in this disclosure, is a profile that summarizes a user's current state of viral infection in themselves and the epidemiology of viruses in the community about the user. A "community," as used in this disclosure, is a particular region of interest for viral epidemiology; a community may include varying degrees of granularity depending on the region selected (town, city, county, state, country, etc.). Viral epidemiological profile 112 may include at least an epidemiological factor, A "epidemiological factor," as used in this disclosure, is a quantitative metric that encapsulates epidemiology of a virus-user relationship. Viral epidemiological profile 112 may include qualitative and/or quantitative parameters which capture the presence of clinical manifestation of viral infection in the user, as well as the detection of and incidence of viral infection in the community. Viral epidemiological profile 112 may include qualitative determinations, such as binary "yes"/"no" determinations for viral infection types, "normal"/"abnormal" determinations about the presence of and/or concentration of viral biomarkers 108, for instance as compared to a normalized threshold value of a viral biomarker 108 among healthy adults. Viral epidemiological profile 112 may include a plurality of epidemiological factors, wherein epidemiological factors are quantitative determinations such as a "viral infection score", which may include any metric, parameter, or numerical value that communicates a viral state. Viral epidemiological profile 112 may include epidemiological factors that are mathematical representations of the current state of viral infection, such as a function describing the viral infection risk as a function of time (with age, changing diet, sleep patterns, time of year, climate, etc.). Epidemiological factors may be virus-specific, climate-specific, tissue-specific, biological pathway-specific, etc. Viral epidemiological profile 112 may include instantaneous viral infection risk, such as weekly, monthly, annual, etc., classified by virus/infection type, according to medical history, biological extraction test result, and the like.

Continuing in reference to FIG. 1, viral epidemiological profile 112 may include a plurality of epidemiological factors involving viral epidemiology for a plurality of viruses, including: 1) detection of virus, 2) targeting of virus, 3) transmission chain, and 4) spread, among other factors. Detection of virus may include tracking of case numbers by testing such as PCR, ELISA, antibody, etc., and/or metagenomic sequencing methods which matches a disease to a viral identity. Targeting of virus may include targeted sequencing from additional human cases and from related viruses uncovering the likely animal reservoir, the time period that it was introduced into the human population, and confirmation about subsequent transmission (e.g. human-to-human, animal-to-human, etc.). Transmission chain may include more intensive virus genome sequencing used to construct detailed transmission chains and identify potential control measures. Spread may include layering additional climatic, transportation, geographic, economic, and demographic data into a large phylogenetic dataset revealing the risk factors that facilitate local and global spread and how this may relate to a user's viral infection risks. This may include training a machine-learning model to build a phylogenetic model which has viral incidence mapped as a function of strain-disease relationships. Spread may use sampling of data, for instance from the Internet, to determine if a viral outbreak is imminent, occurring, etc. Viral epidemiological profile 112 may include modeling disease spread to symptom and to diet to reverse symptomology, improve immunity, and prevent viral infection to build a viral alleviation program, as described in further detail below.

Continuing in reference to FIG. 1, retrieving viral epidemiological profile 112 may include receiving viral epidemiological profile training data. "Viral epidemiological profile training data," as used in this disclosure, is training data sets used for training a machine-learning process, algorithm, and/or model, for the purpose of deriving a viral epidemiological profile of a user. Viral epidemiological profile training data may include viral biomarkers 112 organized into training data sets, as described above. Viral epidemiological profile training data may originate from the user input, for instance via an interaction with computing device 104, to provide medical history data. Viral epidemiological profile training data may originate from a set of users, for instance test result data among the city, state, county, etc., from Center for Disease Control (CDC), municipal health departments, and the like. Viral epidemiological profile training data may include receiving whole genome sequencing, gene expression patterns, and the like, for instance as provided by a genomic sequencing entity, hospital, researchers, database, etc. Viral epidemiological profile training data may be recorded and transmitted to computing device 104 via a wearable device such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like, which may help transmit user symptomology prior to user realization, such as increases and/or decreases in blood pressure, resting heart rate, oxygenation, etc. Training data may originate from an individual other than user, including for instance a physician, lab technician, nurse, epidemiologist, researcher, and the like. Viral epidemiological profile training data may include a plurality of data entries of viral biomarkers for instance as categorized by user cohort—i.e. HPV-positive users, Hepatitis C-positive users, HIV-positive users, users in high viral incidence, low viral incidence, overweight users, users with high fitness levels, immunocompromised users, etc. Such training data may be used to compare user to more accurately define parameters in viral epidemiological profile 112 relative to the overall population.

Continuing in reference to FIG. 1, in non-limiting illustrative examples, training data as described herein, may be input into computing device 104 for instance via a health state questionnaire for onboarding of user symptomology, via any graphical user interface. A "graphical user interface," as used in this disclosure, is any form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction (such as a questionnaire, embedding a hyperlink, uploading a document, etc.) with a user device. A user device, as described in further detail below, may include computing device 104, a "smartphone," cellular mobile phone, desktop computer, laptop, tablet computer, internet-of-things (JOT) device, wearable device, among other devices. User device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, retrieving viral epidemiological profile 112 may include training a viral epidemiological profile machine-learning model with training data that includes a plurality of data entries wherein each entry correlates viral biomarkers 108 to a plurality of epidemiological factors. Viral epidemiological profile machine-learning model 116 may include any machine-learning algorithm (such as K-nearest neighbors algorithm, lazy naïve Bayes algorithm, etc.), machine-learning process (such as supervised machine-learning, unsupervised machine-learning), or method (such as neural nets, deep learning, etc.). Viral epidemiological profile machine-learning model 116 may be trained to derive the algorithm, function, series of equations, or any mathematical operation, relationship, or heuristic, that may be generated to automatedly accept an input (viral biomarker(s) 108) and correlate, classify, or otherwise calculate an output (viral epidemiological profile 112). Viral epidemiological profile machine-learning model 116 may include individual functions, derived for unique relationships observed from the training data, for instance for each viral biomarker 108. In non-limiting illustrative examples, the expression levels of a variety of cytokines, as identified above, may be retrieved from a database, such as a repository of peer-reviewed research (e.g. National Center for Biotechnology Information is part of the United States National Library of Medicine), and the viral epidemiological profile machine-learning model 116 derived algorithm may observe an average and statistical evaluation (mean±S.D.). And, this may be calculated from the data, across which the user's expression level is compared. In such an example, viral epidemiological profile machine-learning model 116 may derive an algorithm according to the data which may also include a scoring function that demonstrates a relationship for how to arrive at a numerical value score according to the user's level of gene expression (e.g. mRNA transcripts of a cytokine per tissue, the cytokine level in blood, etc.) as it relates to the average and statistical evaluation in normal expression of cytokines, such as interleukins.

Continuing in reference to FIG. 1, viral epidemiological profile 112 may include data regarding a plurality of epidemiological factors. Plurality of epidemiological factors may include the factors, as described above. Epidemiological factors may also include, for instance and without limitation, what virus is causing an outbreak: metagenomic sequencing may be used from patient samples to reveal a novel virus—such as Lujo virus—as the causal virus for an outbreak such as in South Africa in 2008; how is the virus transmitting: for instance, sequencing studies of MERS coronavirus combined with coalescent approaches may show that human outbreaks are driven by seasonally varying zoonotic transfer of viruses from camels; where did the outbreak begin: large-scale sequencing efforts and phylogenetic analyses may show, for instance, that the 2009 influenza A/H1N1 pandemic originated in swine populations from Mexico; what factors drive the outbreak: analysis, for example, of more than 1,600 Ebola virus genomes identified critical factors that contributed to the spread of the virus during the 2013-2016 epidemic in West Africa; how many introductions have there been: sequencing data, for instance, of Zika virus from patients and mosquitos in Florida may show that multiple introduction events of the virus sustained the 2016 outbreak in Miami and surrounding counties; when did the outbreak begin: large-scale metagenomic studies, for instance, may show that the Zika epidemic in the Americas likely started in Brazil more than a year earlier than was initially believed; are outbreaks linked: analysis, for instance, of Ebola virus genomes during the 2013-2016 epidemic may show that the virus may persist for more than a year in survivors, and be responsible for flare-ups of the outbreak via sexual transmission; how is the virus evolving: sequencing studies, for example, during the 2013-2016 Ebola epidemic identified mutations in the virus genome that rapidly rose to a high frequency, compatible with increased fitness; experimental follow-up studies showed that some of those mutations were probably Ebola virus adapting to a new host. Such data, when summarized in viral epidemiological profile 112, may be used to derive novel equations to calculate nutrient amounts, relate nutrient amounts to foods, and time the consumption of the food to increase preparedness in handling viral infection, as described in further detail below more accurately.

Continuing in reference to FIG. 1, viral biomarker 108 may be correlated to a plurality of epidemiological factors without the use of machine-learning process(es). For instance and without limitation, computing device 104 may use a web browser and the Internet to identify a plurality of threshold values of cytokine levels that relate to viral biomarkers 108 in "healthy adults", wherein gene expression values that deviate from such a threshold may indicate a particular viral infection, and the magnitude of deviation relates to the magnitude of a numerical value associated therewith.

Continuing in reference to FIG. 1, retrieving the viral epidemiological profile 112 may include generating the viral epidemiological profile 112 using the viral epidemiological profile machine-learning model 116 and at least a viral biomarker 108. Persons skilled in the art may appreciate that viral epidemiological profile 112 may become increasingly more complete, and more robust, with training data describing larger sets of viral biomarkers 108 in the user, training data describing infection incidence with higher granularity, metagenomic data highlighting strain-disease relationships, etc. Epidemiological factors may be generated for each viral biomarker 108 (or set of biomarkers) as described above; epidemiological factors may be generated for each individual virus (e.g. Rhinovirus), viral strain (e.g. Rhinovirus A 100-103), and/or viral type (e.g. cold viruses). Epidemiological factors may be generated for each time of year, climate, weather, etc. Epidemiological factors may be generated for each white blood cell type (e.g. Neutrophils, Macrophages, Basophils, etc.), or set of white blood cell type, among other factors, where user immunological function is related to risk, incidence, and spread.

Continuing in reference to FIG. 1, viral epidemiological profile machine-learning model 116 may derive a unique equation, algorithm, and/or set of functions for determining individual epidemiological factors. Viral epidemiological profile machine-learning model 116 may derive functions, systems of equations, matrices, variables, etc., that describe and/or incorporate relationships between sets of viral biomarkers 108 (training data), for instance and without limitation, combining the expression level of two or more cytokines, multiplied by scalar coefficients according to the presence of SNPs (single nucleotide polymorphisms) or mutations present in the viral host receptors, dividing by the ratio of phosphorylated-unphosphorylated states, ubiquitinated states, etc., of the cytokines. In such an example, said data may determine if a user is currently experiencing a viral infection, and of which particular infection category. In the full spectrum of cell signaling, maintaining cellular homeostasis, cell division, protein degradation, among other biological phenomenon that may contribute to the progression of viral infection, viral epidemiological profile machine-learning model 116 may derive increasingly complicated algorithms for combining viral biomarkers 108 into epidemiology factors summarized in viral epidemiological profile 112.

Continuing in reference to FIG. 1, computing device 104 is configured to identify, using the viral epidemiological profile 112, a plurality of nutrition elements for the user. A "nutrition element," as used in this disclosure, is an item that includes a nutrient intended to be used and/or consumed by user for treating and/or preventing viral infection. A "nutrient," as used in this disclosure," is a biologically active compound whose consumption is intended for the treatment and/or prevention of viral infection. Nutrition element 120 may include alimentary elements, such as meals (e.g. chicken parmesan with Greek salad and iced tea), food items (e.g. French fries), grocery items (e.g. broccoli), health supplements (e.g. whey protein), beverages (e.g. orange juice), and the like. Nutrition element 120 may be "personalized" in that nutrition elements are curated in a guided manner according to viral epidemiological profile 112, gene expression patterns, viral biomarkers 108, SNPs, the time of year, a viral category (e.g. respiratory infection, common cold, tissue tropism, etc.), and the like. Nutrition element 120 may include supplementary use of oral digestive enzymes and probiotics which may also have merit as antiviral measures. Nutrition elements 120 in a virus prevention diet may include zinc, selenium, vitamin A, vitamin C, vitamin D, vitamin E, cyanocobalamin, N-acetyl-cysteine (NAC), and antioxidants such as the carotenoids (α-carotene, β-carotene, lycopene, lutein, cryptoxanthin). Nutrient elements 120 may contain biological active compounds that are not typically considered vitamins and/or minerals, nor are they intended to provide appreciable amounts of calories, such as phytonutrients and nutraceuticals; for instance allium and bioactive ingredients present in cruciferous vegetables such as broccoli sprouts, a known source of antioxidants such as sulforaphane, which may have therapeutic effects on viral infection. Nutrition elements 120 may include a specific dietary category, such as a "ketogenic diet", "low glycemic index diet", "Paleo diet", and so on.

Continuing in reference to FIG. 1, identifying the plurality of nutrition elements 120 includes assigning the viral epidemiological profile 112 to a viral infection category, wherein the viral infection category is a determination about a current viral epidemiological state of the user. A "viral infection category," as used in this disclosure, is a designation of the current viral epidemiological state of a user and/or the community of the user according to data in the viral epidemiological profile. Viral infection category 124 may differ from viral epidemiological profile 112 in that the viral infection category 124 may include a determination about a user's viral state according to how they may be classified as a function of a subset of user cohort. In non-limiting illustrative examples, viral epidemiological profile 112 may include data indicating a current symptomology of 'dry cough', 'shortness of breath', and 'fever', along with a current incidence rate associated with SARS-Cov-2 virus in the user's county; however, the user may not be diagnosed with COVID-19, in which case the user may be classified to such a viral infection category 124 according to the patterns in symptomology and incidence rate data in the viral epidemiological profile 112 of the user. This may be performed for any number of viral categories, in which the user may be preemptively categorized to a disease category based on the propensity of infection according to the data in the viral epidemiological profile 112. Viral infection category 124 may include any medical, physiological, biological, chemical, and/or physical determination about the current state of a user's propensity for viral infection, including their "current status for viral infection" (HIV, HSV, HPV, Hep A/B/C status, etc.), and projected, future likelihood for viral infection, wherein current viral infection and future likelihood are linked by incidence rates, such as instantaneous rate, future rate, etc. The viral epidemiological profile 112 may include data that summarizes the user's biomarkers, symptomology, rates of infection in the community; whereas the viral infection category 124 is a determination about a probable diagnosis or future diagnosis based on patterns observed in symptoms, biomarkers, rates of infection, and the like, from cohorts of users.

Continuing in reference to FIG. 1, viral infection category 124 may include tissue or organ type, such as "liver virus", "lung virus", etc. Viral infection category 124 may include generic body system classification such as encephalitis, meningitis, Common cold, eye infections, pharyngitis, gingivostomatitis, parotitis, pneumonia, cardiovascular, hepatitis, pancreatitis, myelitis, skin infections, sexually transmitted disease, gastrointestinal, etc. Viral infection category 124 may include a designation regarding a viral category that may not involve a particular tissue such as "Respiratory infection", "Diarrheal Virus", etc. Viral infection category 124 may include designations about a group of viral serotypes such as Coxsackie B virus, a clade of virus such as alpha/beta/gamma Coronavirus, viral strain such H1N1 Influenza A, viral incidence rates (e.g. high daily likelihood of infection, low daily likelihood, etc.), transmission chain (e.g. human-to-human rate, reservoir identity, reservoir-to-human rate, etc.), among other data that may be determined on a per-viral serotype, clade, strain, etc. basis. Viral infection category 124 may include identifiers associated with severity of infection (mortality and/or morbidity), infection rates (rate of infection, IC50, LD50, titers, IFUs/mL, PFU/mL, etc.), survivability (percentiles, etc.), among other data that may be determined on a per-viral infection basis. Viral infection category 124 may include a predictive viral infection classification, where a user does not currently harbor a particular viral infection but may include data that indicates a viral infection category 124 with which they may be most closely categorized to, imminently infected, etc. For instance, a user who has not received a flu shot, who lives in a temperate climate in the Fall season of the Northern Hemisphere, in a community where cold and flu infections have significantly risen (as summarized in the user's viral epidemiological profile 112) may classify an individual to "Common Cold" or "Respiratory Infection" viral infection category 124, despite not currently exhibiting either. Viral epidemiological profile 112 may have associated with it an identifier, such as a label, that corresponds to a viral infection category 124.

Continuing in reference to FIG. 1, assigning the viral epidemiological profile to a viral infection category may include training a viral classifier using a viral classification machine-learning process and training data which includes a plurality of data entries wherein each data entry correlates viral biomarkers 108 to a viral infection category 124. A "viral classifier," as used in this disclosure, is a machine-learning model as defined herein, such as a mathematical model, neural net, or program generated by a machine learning algorithm known as a "classification algorithm," as described in further detail below, that sorts inputs into categories or bins of data, outputting viral infection category 124, or bins of data and/or labels associated therewith.

Continuing in reference to FIG. 1, training viral classifier 128 to classify user to viral infection category 124 may include using a viral classification machine-learning process. Classification may include identifying which set of categories (viral infection category 124) an observation (viral biomarker 108) belongs. Alternatively or additionally, observations associated with epidemiological profile 112 may be classified to viral infection category 124. Viral classifier 128 may include classification based on clustering as a function of pattern recognition, wherein the presence of certain viral biomarkers 108 and/or viral epidemiological factors, such as genetic indicators, symptoms, community incidence, and the like, relate to a particular viral infection category 124. Such classification methods may include binary classification (with or without the use of machine-learning), where the viral epidemiological profile 112 is matched to each existing viral infection category 124 and sorted into a category based on a "yes"/"no" match. Classification done in such a manner may include weighting, scoring, or otherwise assigning a numerical value to elements in viral epidemiological profile 112 as it relates to each viral category and assign a user to a viral infection category 124 for the viral type that results in the highest 'score'. Such a 'score' may represent a "likelihood", probability, or other numerical data that relates to the classification into viral infection category 124.

Continuing in reference to FIG. 1, viral classification machine-learning process may include any machine-learning process, method, and/or algorithm, as described in further detail below. Viral classification machine-learning process 132 may generate a viral classifier 128 using training data. Viral classifier 128 may be configured to output at least a datum that labels or otherwise identifies a set of data that are clustered together, found to be close under a viral infection category 124, among other classification, as described herein. Machine-learning module, as described in further detail below, may generate viral classifier 128 using a classification algorithm, defined as a process whereby a computing device and/or any module and/or component operating thereon derives a classifier from training data. As a non-limiting example, viral epidemiological profile 112 may be used as training data for viral classifier 128 which may be trained to classify elements of training data to elements that characterizes a sub-population, such as a subset of viral biomarker 108 (such as gene expression patterns as it relates to a variety of viral infection types) and/or other analyzed items and/or phenomena for which a subset of training data may be selected.

Continuing in reference to FIG. 1, assigning the viral epidemiology profile 112 to a viral infection category 124 may include assigning the viral infection category 124 as a function of the viral classifier 128. Viral classifier 128 may classify viral biomarker 108 (input) to viral infection category 124 (output) may include assigning the viral infection category 124 as a function of the viral classification machine-learning process 132 and the viral epidemiological profile 112 (e.g. summary of viral biomarker(s) 108, among data originating from outside the user). Training data may include sets of epidemiological factors and/or viral biomarkers 108, as described above. Such training data may be used to "learn" how to categorize a user's viral epidemiological profile 112 to viral infection categories 124 depending on trends in viral biomarkers 108, gene expression, SNPs, user symptomology, rate of incidence, and the like. Such training data may be used to anticipate a type of viral infection (viral infection category 124) from viral epidemiology profile 112 as a viral outbreak threat prior to the outbreak occurring. Training data for such a classifier may originate from user input, for instance via a health state questionnaire via a graphical user interface, may originate from a biological extraction test result such as genetic sequencing, blood panel, lipid panel, etc. Training data may originate from a user's medical history, a wearable device, a family history of disease. Training data may similarly originate from any source, as described above, for viral biomarker 108 and determining viral epidemiological profile 112.

Continuing in reference to FIG. 1, identifying the plurality of nutrition elements 120 includes calculating, according to the viral infection category 124, a plurality of nutrient amounts, wherein calculating a plurality of nutrient amounts includes determining an effect of the plurality of nutrient amounts on the viral epidemiological profile 112. An "effect of a nutrient," as used in this disclosure, is a change, consequence, and/or result in at least a viral biomarker 108, viral epidemiological profile 112, viral infection category 124, and/or likelihood of viral infection in a user due to consumption of an amount of a nutrient. An effect of a nutrient may be "no effect". An effect of a nutrient may include a resultant increase/decrease in viral biomarker 108. An effect of a nutrient may include in increase/decrease in likelihood of viral infection. An effect of a nutrient may include a change in viral infection category 124. Calculating an effect of a nutrient may include determining how a viral biomarker 108 may change, such as an increase/decrease according to a particular amount of nutrient. For instance and without limitation, such a calculation may include determining the effect on cytokine levels from chronic, sustained nutrient amounts in a diet for weeks, months, etc.

Continuing in reference to FIG. 1, determining the effect of the plurality of nutrient amounts on the viral epidemiological profile 112 may include receiving viral spread training data. "Viral spread training data," as used in this disclosure, is data for training a machine-learning process, algorithm, and/or model which includes a plurality of data entries that correlates a plurality of nutrient amounts to viral spread rates in a region. Viral spread training data 136 may be used to determine "idealized nutrient amounts," wherein a machine-learning process may train with such data to derive nutrient amounts, that if consumed by the population at large, may reduce overall spread of a virus through that population. Viral spread training data 136 may include any type of training data described herein, for instance viral biomarkers 108 for a user, subset of users, incidence of a virus in a community over time, etc. Viral spread training data 136 may include any data concerning the epidemiological factors, such as data of positive cases of viral infection per number of individuals tested originating from municipal health departments, clinics, Centers for Disease Control (CDC), hospitals, and the like, as described herein. Viral spread training data 136 may include data concerning the use of public transit systems. In non-limiting illustrative examples, such training data may include the number of individuals who use the subway, buses, aircraft, etc., in a region related to the number of positive cases of a viral outbreak in the region. Such training data may be used to derive relationships from the data that corresponds to spread of a virus, wherein each type of transit has a particular risk factor.

Continuing in reference to FIG. 1, determining the effect of the plurality of nutrient amounts on the viral epidemiological profile 112 may include a hypothesis (model) about the user's health after consuming a nutrient amount. An effect of a plurality of nutrient amounts may include the effect on viral infection category 124 (e.g. changing from "Common Cold" to "Respiratory Virus"), viral biomarker 108 (e.g. decreasing amounts of cytokines, etc.), likelihood of viral infection (e.g. 60% to 20% chance), risk (very high, high, medium, etc.), and the like, from a particular nutrient amount, or combination of nutrient amounts. In non-limiting illustrative examples, determining an effect of a nutrient may include determining if a change in viral infection category 124 may arise from adding and/or removing a nutrient from a user's diet, for instance changing a viral infection category 124 from "Common Cold" to "Respiratory Virus," as increasing dietary vitamin C, zinc, and vitamin D may reduce risk from Rhinoviruses, Parainfluenza viruses, RSV, etc., but due to weather, climate, and incidence, user remains in "Respiratory Virus" category due to Influenza, Adenovirus, Coronavirus.

Continuing in reference to FIG. 1, determining the effect of the plurality of nutrient amounts on the viral epidemiological profile 112 may include generating a spread model, wherein the spread model is a machine-learning model trained with the viral spread training data 136 which includes a plurality of data entries that models a plurality of effects of the plurality of nutrient amounts on viral spread rates. A "spread model," as used in this disclosure, is a machine-learning model generated from viral spread training data 136, which includes the phylogenetics and epidemiology of a virus in a human population. Spread model 140 may include "idealized" viral epidemiology modeling, wherein the rates of spread of a viral outbreak are tested against varying nutrient consumption in the population. In non-limiting illustrative examples, spread model 140 may derive a series of function that calculates how an individual's risk of infection changes if the population met a particular nutrition amount thresholds. In such an example, nutrient amounts at local minima of the functions may represent the most reduced viral risk for those nutrients.

Continuing in reference to FIG. 1, determining the effect of the plurality of nutrient amounts on the viral epidemiological profile 112 may include determining the effect of the plurality of nutrient amounts as a function of the spread model 140. Spread model 140 may be increasingly robust, in that it may include retrieving and incorporating overlaid data structures relating public transportation, weather and climate, rates of incidence of a particular virus, such as COVID-19 (SARS-CoV-2 viral strain responsible for 2020 pandemic), among other types of data, to generate a model of the spread of the virus in a community. Such a spread model 140 may be used to inform nutrient amounts and timing of nutrient consumption due to the effect of nutrients on the spread of a virus (population phylogenetics—i.e. if x nutrient is consumed among population, spread is reduced by y amount). Alternatively, spread model 140 may be used to optimally time nutrient consumption by an amount—e.g. within 24 hrs. of case spike, following week of temperature below 60 degrees Fahrenheit, etc., to best prevent infection. Spread model 140 output may include mapping a series of points, such as numerical values per county in the United States, overlaid over a regional map. Each county may have a value assigned associated with the active number of cases of a viral outbreak, weather conditions conducive to viral spread (e.g. temp, humidity), population density, etc. Spread model 140 may incorporate these values, for instance as variables in a function, wherein spread model 140 may solve for a series of values, or singular value, which may be presented geographical using a mapping application, such as a heat map over a 500 mile radius. In such an instance, spread model 140 may be trained with data as each day passes to accurately derive how each variable affects the number of cases in each succeeding day.

Continuing in reference to FIG. 1, computing device 104 is configured for calculating the plurality of nutrient amounts as a function of the effect, wherein the plurality of nutrient amounts is a plurality of amounts intended to result in prevention of a viral infection. A "nutrient amount," as used in this disclosure, is a numerical value(s) relating to the amount of a nutrient. Nutrient amount 144 may include mass amounts of a vitamin, mineral, macronutrient (e.g. grams carbohydrate, protein, fat), a value of calories, mass amounts, units, and/or concentrations of phytonutrients, antioxidants, pharmaceuticals, bioactive ingredients, and the like.

Continuing in reference to FIG. 1, calculating the plurality of nutrient amounts may include determining the plurality of nutrient amounts as a function of at least a viral biomarker 108 and the plurality of effects. Determining a nutrient amount may include a mathematical operation, such as subtraction, addition, etc. For instance and without limitation, spread model 140 may be used to derive an effect wherein a +5 mg daily nutrient amount of a vitamin combination results in a 10% decreased risk of viral infection, up to +40% benefit; in such an instance, a maximal benefit may be found, and nutrient amount calculated. Determining a nutrient amount may include retrieving an empirical equation that describes relationships between a nutrient and viral biomarker 108, test results, climate, and viral spread, etc. Determining a nutrient amount may include deriving an algorithm, function, or the like, to generate a plurality of nutrient amounts more accurately as a function of the viral epidemiological profile 112.

Continuing in reference to FIG. 1, computing device 104 may calculate nutrient amounts 144, for instance, by retrieving a default amount, such as from a standard 2,000 calorie diet, and modifying the amount according to viral epidemiological profile 112. Such a calculation may include a mathematical operation such as subtraction, addition, multiplication, etc.; alternatively or additionally, such a calculation may involve deriving a loss function, vector analysis, linear algebra, system of questions, etc., depending on the granularity of the process. Deriving such a process for calculating nutrient amounts 144 may include machine-learning. Nutrient amounts 144 may include threshold values, or ranges of values, for instance and without limitation, between 80-120 mg vitamin C per 24 hours, wherein the minimal acceptable blood concentration of ascorbic acid must stay above 8 mg/L (according to viral epidemiological profile 112). Nutrient amounts 144 may then be calculated as, for instance using banding, where each datum of viral epidemiological profile 112 elicits a particular numerical value range of nutrient amount 144 or combinations of amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutrient amounts, for instance in a database. The amounts may be re-calculated and converted according to a user's viral epidemiological profile 112. For instance, these amounts may relate to an average BMI, adult male, in a heavily populated area experiencing high numbers of Rotavirus. In this case, the amounts may be adjusted according to unique user-specific viral epidemiology profile 112, and an equation derived by machine-learning may be used to "learn" which amounts to increase, and which to decrease. In non-limiting illustrative examples, an obese woman who was recently placed on a 1,400 Calorie/day diet, and not may require the above amounts and per-user amounts may be recalculated according to such a diet, where some amounts may increase, some may decrease, and some may remain constant. For instance, if such a person were prone to viral infection due to nutrition deficiency, a particular increase among vitamin C, zinc, vitamin E, and vitamin A may be calculated according to a weighting factor associated with such a pattern of input data.

Continuing in reference to FIG. 1, calculating nutrient amounts 144 may include deriving a weighting factor to adjust, or otherwise re-calculate, an amount. Weighting factor may be determined by computing device 104, for instance, by querying for vitamin amounts according to data inputs identified in the viral epidemiological profile 112.

Continuing in reference to FIG. 1, calculating nutrient amounts 144 may include generating training data using the plurality of effects of the plurality of nutrient amounts 144 identified according to the viral infection category 124. For instance and without limitation, generating training data may include searching, using a web browser and the Internet, to locate nutrient amount 144 relating to viral infection category 124. Generating training data may include retrieving effect output by spread model 140. Training data for deriving nutrient amounts 144 may include viral spread training data 136. Viral spread training data 136 for calculating nutrient amounts 144 may include immunological, clinical, and viral infection pathology outcomes as a function of nutrient supplementation in a variety of specifics cases (cohort age, virus type, time of year, starting deficiency level, etc.).

Continuing in reference to FIG. 1, calculating nutrient amounts 144 may include training a nutrition machine-learning model according to the training data, wherein training data includes a plurality of data entries that correlates the magnitude of nutrient effect to a plurality of nutrient amounts for each viral infection category 124. Nutrition machine-learning model 148 may include any machine-learning process, model, method, and/or algorithm as described herein, that may be performed by machine-learning model, as described in further detail below. Nutrition machine-learning model 148 may be trained with training data, as described herein, to derive a dosage-based effect (mathematical function) for a plurality of nutrients (values) according to viral infection category 124. In such a case the machine-learning model may accept an input of a viral infection category 124, such as an anticipated viral infection, and then output nutrient amounts 144, which may include effects, nutrient identities, nutrient combinations, and specific per-user amounts.

Continuing in reference to FIG. 1, for example in non-limiting illustrative examples, training data for nutrition machine-learning model 148 may include vitamin A supplementation from animal models which may result in higher serum anti-rabies immunoglobin (IG) (2.1 times) than those without supplementation, supporting the supplementation of vitamin A for boosting immunological function in individuals with high rabies incidence. Supplementation of vitamin A in combination with vitamin D in children with insufficient or deficient levels of RBP (vitamin A) and 25-hydroxyvitamin D (vitamin D) may result in greater antibody responses (IG concentration). Such data may be used to derive, for instance and without limitation, a function for a particular increases (e.g., mg/kg body weight) of vitamin A/vitamin D combination dosage and frequency. Training data may include serum levels of the vitamins, and their associated vitamers in the blood (carotenoids, calcitriol, etc.), as a function of supplementation, versus immunological response to virus. Such training data may exist for individual classes of IGs (e.g., IgG, IgM, IgA, etc.), particular viral infection categories 124, age, and the like. Accordingly, training data may be organized by a classifier, which classifies data into subsets according to similarity, cohort grouping, etc., as described in further detail below. Training data may be used, for instance, to train nutrition machine-learning model 148 to derive per-user equations, functions, etc., for calculating efficacious nutrient amounts 144, as it may relate to individual virus families, viral infection categories 124, etc.

Continuing in reference to FIG. 1, in further non-limiting illustrative examples, training data for nutrition machine-learning model 148 may include data describing that significantly more Hepatitis C virus patients (HCV+) were HSV-RNA negative (at week 4, 12 and 24), wherein vitamin D supplementation may have been strongly and independently associated with sustained virological response in multivariate analysis. Additionally, ninety-five percent in the vitamin D supplemented cohort were HCV-RNA negative at week 4 and 12. At 24 weeks (approximately 6 months) sustained virological response was significantly more in supplemented group. In such an example, logistic regression analysis may identify vitamin D supplement as an independent predictor of viral response. Although clinically may not be true for all viral infection categories 124, as no significant difference in incidence of wintertime upper respiratory tract infections may be observed in those with vitamin D supplemented diets than compared to standard amounts of vitamin D. It is thought that higher than recommended dosages may not hold a benefit for the Hepatitis viral infection categories 124, but normal vitamin D supplementation may remain beneficial in those than vitamin D deficiency. Although, vitamin D supplemented cohorts may have shown a higher TGFβ plasma level (viral biomarker 108) in response to influenza vaccination without improved antibody response; vitamin D may have a function in directing lymphocyte (white blood cell) polarization toward a tolerogenic immune response. In such an instance as vitamin D, a relationship may be uncovered using nutrition machine-learning model 148 trained with the above training data, that supplementation of a particular vitamin only holds benefit if a deficiency is found, and otherwise not helpful to supplement at certain times of the year, for certain virus types, or for those with varying degrees of deficiency. Additionally, it may be found that nutrient amounts 144 are highly user-dependent where incidence of virus (such as the case with COVID-19), access to vaccination, weather, climate, population density may all represent confounding variables in any function derived with machine-learning. Such variables may be encapsulated and mathematically described in spread model 140, as spread model 140 informs effects of nutrients for such variables; whereas, calculated nutrient amounts may be generated by nutrition machine-learning model 148.

Continuing in reference to FIG. 1, in additional non-limiting illustrative examples, training data for nutrition machine-learning model 148 may include positive effects of vitamin E supplementation as observed in the treatment of chronic Hepatitis B in a small pilot randomized control trial (RCT), where a significantly higher normalization of liver enzymes (ALT/AST, viral biomarkers 108) and HBV-DNA negativization (viral biomarker 108), may be observed in the vitamin E supplementation group. Similar results may be observed in an RCT in, for instance, the pediatric population, where vitamin E treatment resulted in a higher anti-HBV seroconversion and virological response. However, vitamin E supplementation may not have an effect on the risk of pneumonia in participants with body weight in a range from 70-89 kg, while vitamin E increased the risk of pneumonia in participants with body weight <60 kg, participants with body weight >100 kg, and with smokers aged 50-69 yrs. The harm of vitamin E supplementation, however, may be observed to be restricted to participants with dietary vitamin C intake above the median. Simply increasing supplementation generically among nutrient amounts 144 may not result in improved viral infection prevention, and in some cases may cause harm to the user. In such an instance, training data is particularly important for deriving per-user nutrient amounts 144 to achieve any intended viral infection prevention efficacy. Although rarely is a single nutrient ever being consumed individually. Persons skilled in the art may appreciate that with greater variety of nutrients, supplementation becomes increasingly complex.

Continuing in reference to FIG. 1, in further non-limiting illustrative examples, training data for nutrition machine-learning model 148 may include correction of specific nutrient combination deficiencies (e.g. zinc, selenium sulfide, beta carotene, ascorbic acid, and vitamin E). Supplementation may be observed after 6 months (post supplementation) and may be maintained throughout the first year, during which there may be no effect on delayed-type hypersensitivity (DTH) skin response; however, the number of patients without respiratory tract infections during the supplementation period may be higher in groups that received the combinatorial nutrient supplementation. Immunologically, antibody titers (IG concentration) after influenza vaccination may be higher in groups that received combination trace element supplementation alone or associated with vitamins, whereas the vitamin group (vitamin supplementation alone) may have significantly lower antibody titers. Moreover, neither daily multivitamin mineral supplementation at physiological dose, nor 200 mg of vitamin E (alone), showed a favorable effect on incidence and severity of acute respiratory tract infections in well-nourished, non-institutionalized elderly individuals. Training data in the form of vitamin supplementation versus immunological responses may be used to derive nutrient relationships between combinations of supplements. Such relationships may show that certain nutrients may not need to be increased, or that different nutrients may need to be increased as a function of viral epidemiological profile 112 (age, institutionalization) and viral infection category 124 (antibody type, vaccination possible, etc.).

Continuing in reference to FIG. 1, in non-limiting illustrative examples, vitamin A is a fat-soluble vitamin, which is crucial for maintaining vision, promoting growth and development, and protecting epithelium and mucosal integrity in the body. It is known to play an important role in enhancing immune function and having a regulatory function in both cellular and humoral immune responses. Vitamin A supplementation to infants may show the potential to improve antibody response after some vaccines, including measles and anti-rabies vaccination. Correspondingly, an enhanced immune response to influenza virus vaccination may also be observed in children (2-8 years) who were vitamin A and D-insufficient at baseline, after supplementation with vitamin A and D. Vitamin D, another fat-soluble vitamin, also plays a vital role in modulating both innate and adaptive immune responses. Epidemiological data has linked vitamin D deficiency to increased susceptibility to acute viral respiratory infections. Possible mechanisms may suggest that vitamin D plays an important modulatory role of the innate immune responses to respiratory viral infections, such as Influenza A and B, parainfluenza 1 and 2, and Respiratory syncytial virus (RSV). A systematic review on the role of vitamin D in the prevention of acute respiratory infections, which included 39 studies (4 cross-sectional studies, 8 case-control studies, 13 cohort studies and 14 clinical trials), noted that observational studies predominantly report statistically significant associations between low vitamin D status and increased risk of both upper and lower respiratory tract infections. However, results from RCTs included in the above systematic review were conflicting, possibly, reflecting heterogeneity in dosing regimens and baseline vitamin D status in study populations. Few RCT have been conducted subsequent to the above systematic review. A study on the effect of high-dose (2000 IU/day) vs. standard-dose (400 IU/day) vitamin D supplementation on viral upper respiratory tract infections did not show any significant difference between the two group. However, only about ⅓ of the study population had vitamin D levels <30 ng/ml. Similarly in another RCT, a monthly high-dose (100,000 IU/month) vitamin D supplementation reduced the incidence of acute respiratory infections in older long-term care residents, in comparison to a standard dose group (12,000 IU/month). It is evident that vitamin D supplementation may play a role in antiviral immunity. Furthermore, vitamin D has demonstrated a beneficial effect in other viral infections, for example adding vitamin D to conventional Peg-α-2b/ribavirin therapy for treatment-naïve patients with chronic HCV genotype 1 infection significantly improved the viral response, and a similar effect may also be observed in patients with HCV genotype 2-3.

Continuing in reference to FIG. 1, computing device 104 may calculate nutrient amounts 144 as a function of the nutrition machine learning model 148 and the per-user pharmacokinetics. For instance and without limitation, using training data such as described herein, computing device 104 may calculate nutrient amounts 144 by determining differences in nutrient quality from organic sources (food items) from nonorganic sources (commercially-available supplements) from a bioavailability standpoint. Per-user pharmacokinetics, rates of metabolism and/or adsorption of nutrients amounts 144 may differ among user cohorts, which may negate the effectiveness of proscribing particular diet types and nutrition amounts 144 to users. In such an instance, computing device 104 may account for such details using nutrition machine-learning model 148, trained with training data as described above, to derive equations, functions, and/or mathematical relationships observed in the training data to calculate more accurate and specific nutrient amounts 144.

Continuing in reference to FIG. 1, in non-limiting illustrative examples, nutrition machine-learning model 148 may be used to derive per-user pharmacokinetics of vitamin B6. The machine-learning algorithm may accept training data including a plurality of data values, for instance, the total amount of protein consumed (in grams) and total amount of vitamin B6 consumed (in mg) per day in a diet, and what the serum levels of the vitamin B6 vitamer, pyridoxal-5-phosphate, over the course of a month, and derive the rates of metabolism, or how 'well' the user is obtaining the vitamin from nutrition elements and adsorbing vitamin B6. In other words, the machine-learning algorithm may derive a function (e.g. using linear regression, vector quantization, least squares, etc.) that describes the pharmacokinetics for that particular user regarding what amount of vitamin B6 consumed, per amount of dietary protein, results in what corresponding amount of bioactive vitamin compound. Such a mathematical relationship, obtained from a machine-learning model and the training data, may then be used by computing device 104 with an input of the viral epidemiological profile 112, which enumerates the amount viral biomarkers 108 (e.g. cytokine level) and/or incidence of infection, spread rates, etc., to calculate an output which is a more accurate, customized, per-user nutrient amount 144 of vitamin B6 that is curated to specifically prevent viral infection, reduce daily risks of infection, etc., according to user-specific data. Persons skilled in the art may appreciate that this process may be repeated and completed for the full spectrum of nutrients, both required as part of a diet and not required as part of a diet.

Continuing in reference to FIG. 1, computing device 104 may calculate nutrient amounts 144 as a function of the nutrition machine learning model 148 and the viral infection category 124. Computing device 104 may 'learn' how to more accurately calculate the amounts by which to decrease, supplement, and/or omit items from a viral infection program. Spread model 140 may relate predicted nutrition effects to viral infection category 124 as a function of the epidemiology of a particular virus, or class of viruses. These effects may be generated as labels, identifiers, and/or any other relating data structure that is associated to viral infection category 124. Nutrition machine-learning model 148 may train with training data, such as described herein, which relates viral infection categories 124 (and associated effects) to specific nutrition amounts 144. This way highly correlated effects and accurate nutrient amounts 144 may be derived for each user, regardless of age, lifestyle, virus type, and other epidemiological factors. Such nutrient amounts 144, as derived by system 100, may be stored and/or retrieved from a database. Persons skilled in the art may appreciate that system 100 may generate a highly-specific, yet varied spectrum of personalized nutrient amounts with increased participation among users.

Continuing in reference to FIG. 1, calculating personalized nutrient amounts 144 may include using nutrition machine-learning model 136 to generate a function (or series of functions) describing nutrient amounts 144 calculated prior to classification to viral infection category 124. In non-limiting illustrative examples, it may be shown that fiber content, which is oftentimes classically reported in a generic sense as "carbohydrates", is important for particular gastrointestinal viral infections. Patterns may identify, for instance, that plant-based diets, supplemented with particular bacterial species of probiotics may result in personalized nutrient amounts 144 for viral epidemiological profiles 112 classified to those viral infection categories 124. Such a relationship found in training data may be derived and captured in a mathematical relationship, such as a function or equation, and stored prior to any proper "gastrointestinal viral infection" classification has been made. This way, nutrient amounts 144, and corresponding nutrition elements 120 may be retrieved, for instance using a classification algorithm, by retrieving data once a user has been classified to such a viral infection category 124.

Continuing in reference to FIG. 1, calculating nutrient amounts 144 may include calculating nutrient amounts 144 as a function of the nutrition machine learning model 148 and the viral infection category 124. Trained nutrition machine learning model 148 may accept an input of viral epidemiological profile 112 (and associated viral infection category 124) to output nutrient amounts 144. Nutrient amounts 144 may be calculated using a variety of functions, systems of equations, and the like, derived from mathematical relationships and/or heuristics identified in training data, for instance from nutrition elements 120 identified directly from viral infection categories 124. Persons skilled in the art may appreciate that each viral infection category 124, of the 100's+ different types of viral infections, may have a unique algorithm for calculating nutrient amounts 144, of the 100's+ of distinct nutrients (and combinations thereof) identified. For instance and without limitation, each virus type, tissue/organ type, stage of viral outbreak, age of person, viral biomarker 108, viral epidemiological profile 112, etc., may elicit a different mathematical equation for calculating vitamin C. Wherein, vitamin C is one of many water-soluble vitamins, and that each vitamin of that class may have a different equation associated with calculating nutrient amounts 144. Each equation may be derived by nutrition machine learning model 148 according to the training data. Additionally, each user's specific pharmacokinetics, current dietary patterns, and the like, may add a unique step in the calculation, wherein the calculated nutrient amount 144 is further personalized.

Continuing in reference to FIG. 1, identifying the plurality of nutrition elements 120 includes identifying, as a function of the plurality of nutrient amounts 144, the plurality of nutrition elements 120, wherein the plurality of nutrition elements 120 are intended to prevent viral infection as a function of the viral infection category 124. Viral epidemiological profile 112 may be associated with user that does not currently have a viral infection belonging to viral infection category 124. In such an instance, nutrition elements 120 may be "personalized" to an individual in that they are intended to prevent, as described above, viral infection in that individual. Nutrition element 120 may prevent viral infection in that they provide a nutrient intended to meet individualized, calculated nutrient amounts 144. Nutrient element 120 may prevent viral infection in addressing nutrient deficiencies, surplus, and the like. Nutrition element 120 may include foods and supplements intended to address genetic and viral biomarker 108 issues that are unique to each individual. "Curating" nutritional elements 120, as used in this disclosure, is a process of combining ingredients and/or nutrients according to calculated nutrient amounts 144. Curated nutritional elements 120 may include combining ingredients such as spices, plant-based materials, animal products, probiotic cultures, and the like, to result in a custom nutritional element 120, such as a particular "health shake", unique dish, or the like, that may not be available commercially.

Continuing in reference to FIG. 1, computing device 104 is configured to identify, as a function of the calculated nutrient amounts 144, the plurality of nutrition elements 120, wherein the plurality of nutrition elements 120 may be intended to address a datum in the viral epidemiological profile 112. Nutrition elements 120, "intended to address a datum in the viral epidemiological profile 112," may refer to the process(es) of viral infection treatment, recovery, and/or prevention. "Viral infection treatment," as used in this disclosure, is the amelioration of viral infection symptomology; such as nutrition elements 120 intended for a person with fever, cough, runny nose, chills, etc. "Viral infection prevention," as used in this disclosure, is the reduction in risk for viral infection. Viral infection prevention may include specifically curated nutrition elements 120 according to relationships regarding the risk of viral infection, wherein the risk may be decreased if nutrient targets are achieved, and risk may increase quicker then expected according to epidemiological factors.

Continuing in reference to FIG. 1, identifying the plurality of nutrition elements 120 includes identifying the nutrition elements 120 according to the viral infection category 124. Identifying nutrition element 120 according to viral infection category 124 may include querying, for instance using a web browser and the Internet, for foods, supplements, bioactive ingredients, and the like, which are correlated with a particular viral infection category 124. For instance and without limitation, computing device 104 may organize a search for nutrition elements 120 intended for "Cardiovascular Viral Infection", wherein an entire diet may be crafted around target nutrient amounts 144 and the categorization of the viral epidemiological profile 112 to "Cardiovascular Viral Infection". In such an example, the nutrition elements 120 are outputs generated from an input search criteria of "Cardiovascular Viral Infection". The output elements become "personalized" as they are arranged into daily, weekly, monthly, etc., individual meals and/or meal schedule according to a user's particular calculated nutrient amounts 144. The viral infection category 124 may serve as a filtering step, wherein a search is guided by the viral epidemiological profile 112 as it was classified to a viral infection category 124.

Continuing in reference to FIG. 1, computing device 104 may identify the plurality of nutrition elements 120 by using nutrient amount 144 as an input and generating combinations, lists, or other aggregates of nutrition elements 120 necessary to achieve nutrient amount 144. For instance, computing device 104 may use a template nutrient amount 144 of '200 mg vitamin C' and build a catalogue of nutritional elements 120 until the 200 mg vitamin C value is obtained. Computing device 104 may perform this task by querying for food items, for instance from a menu, grocery list, or the like, retrieving the vitamin C content, and subtracting the value from the nutrient amount 144. In non-limiting illustrative examples, computing device 104 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 104 may search according to a set of instructions (e.g. food preferences, allergies, restrictions, etc.) present in a viral epidemiological profile 112, provided by a physician, user, or the like, and subtract each identified nutrition element 120 nutrient amount from nutrient amount 144 until a combination of nutritional elements 120 that represents a solution is found. Once a solution is found, computing device 104 may generate a file of nutrition elements 120 and store in a database, as described in further detail below.

Continuing in reference to FIG. 1, generating combinations of nutrition elements 120 to achieve nutrient amounts 144 may include generating an objective function. An "objective function," as used in this disclosure, is a mathematical function that may be used by computing device 104 to score each possible combination of nutrition elements 120, wherein the objective function may refer to any mathematical optimization (mathematical programming) to select the 'best' element from a set of available alternatives. Selecting the 'best' element from a set of available alternatives may include a combination of nutrition elements 120 which achieves the nutrient amounts 144 in addressing viral epidemiological profile 112 in a user.

Continuing in reference to FIG. 1, in non-limiting illustrative examples, an objective function may include performing a greedy algorithm process. A "greedy algorithm" is defined as an algorithm that selects locally optimal choices, which may or may not generate a globally optimal solution. For instance, computing device 104 may select combinations of nutrition elements 120 so that values associated therewith are the best value for each category. For instance, in non-limiting illustrative example, optimization may determine the combination of the most efficacious 'serving size', 'timing of consumption', 'probiotic product', 'vegetable', etc., categories to provide a combination that may include several locally optimal solutions but, together, may or may not be globally optimal in combination.

Still referring to FIG. 1, in further non-limiting illustrative examples, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user (e.g. lactose intolerance, poor absorption, food allergy, user preference, etc.), and a linear program may use a linear objective function to calculate ingredient combinations, considering how these limitations effect combinations. In various embodiments, system 100 may determine a set of instructions towards addressing a subject's viral epidemiological profile 112 that maximizes a total viral infection prevention score subject to a constraint that there are other competing objectives. For instance, if achieving one nutrient amount 144 by selecting from each nutrition element 120 may result in needing to select a second nutrition element 120, wherein each may compete in viral infection prevention (e.g. adopting two or more diet types simultaneously may not be feasible, a vegan option and a non-vegan option, etc.). A mathematical solver may be implemented to solve for the set of instructions that maximizes scores; mathematical solver may be implemented on computing device 104 and/or another device in system 100, and/or may be implemented on third-party solver.

With continued reference to FIG. 1, in further non-limiting illustrative examples, objective function may include minimizing a loss function, where a "loss function" is an expression of an output which a process minimizes to generate an optimal result. For instance, achieving nutrient amounts 144 may be set to a nominal value, such as '100', wherein the objective function selects elements in combination that reduce the value to '0', wherein the nutrient amounts 144 are '100% achieved'. In such an example, 'maximizing' would be selecting the combination of nutrition elements 120 that results in achieving nutrient amounts 144 by minimizing the difference, where suboptimal pairing results in score increases. As a non-limiting example, computing device 104 may assign variables relating to a set of parameters, which may correspond to viral infection prevention components, calculate an output from a mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 is configured to generate, using the plurality of nutrition elements 120, the viral alleviation program. A "alleviation program," as used in this disclosure, is a collection of nutrient amounts 144 and nutrition elements 120 organized into a frequency (timing) and dosage (serving size) schedule. Alleviation program 152 may include a remedy after viral infection. Alleviation program 152 may include a nutrition element intended to prevent viral infection as a prophylaxis. Alleviation program 152 may include gathering, classifying, or otherwise categorizing nutrient amounts 144, nutrition elements 120 lists, or the like, which incorporates virus-specific recommendations. For instance, nutrition elements 120 may be scored with a numerical score scale that associates a meal, beverage, supplement, etc., with preventing infection, benefit to virus-infected patient, and the like. Alleviation program 152 may include selecting nutrition elements 120 according to a threshold score, where items above the threshold are selected and arranged. Threshold score may include a daily threshold, wherein nutrition elements 120 are selected each day according to the threshold; and threshold may include a numerical value relating to infection prevention, nutrient amount 144, among other outputs of system 100 described herein. Determining alleviation program 152 may include machine-learning. For instance, training a machine-learning model to identify a scoring rubric for building the alleviation program 152 based on some criteria such as infection prevention, minimizing daily risk, in response to viral outbreak, epidemiological factors, spread model 140, among other criteria. Alleviation program 152 may relate specific viral strains to specific nutrients of interest and provide nutrition element 120 scheduling times and serving sizes for each meal. Alleviation program 152 may differ from one user to the next according to the magnitude of the disease outline (viral infection category 124 and viral epidemiological profile 112).

Continuing in reference to FIG. 1, generating the viral alleviation program 152 may include generating a alleviation program classifier using a nourishment classification machine-learning process to classify the plurality of nutrient amounts 144 to the plurality of nutrition elements 120, and outputting the plurality of nutrition elements as a function of the alleviation program classifier. Alleviation program classifier 156 may include any machine-learning model generated by a classification machine-learning process, as described herein, performed by a machine-learning module as described in further detail below. Training data for alleviation program classifier 156 may include any training data, as described herein, which may be used to classify nutrient amounts 144 to nutrition elements 120. Such training data may include nutrition facts of food items, supplements, etc., which may be modified by per-user pharmacokinetics to derive product-specific nutrient amounts 144 for each nutrition element 120. Alleviation program classifier 156 may accept an input of nutrient amounts 144 and output a plurality of nutrition elements 120 with associated frequency (timing) and dosage (serving size) schedule according to relationships between nutrition elements 120 and nutrient amounts 144. For instance and without limitation, alleviation program classifier 156 may contain relationships between individual fruits and vegetables, that when more vegetables are selected, certain fruits may not be necessary to schedule within the same timeframe (day, meal, etc.). Such a classification process may determine a function, system of equations, and the like, which may be solved for in determining which nutrition elements 120 (fruits, vegetables, meats, dairy, grains, etc.) are useful to obtaining the nutrient amounts 144, while not missing some lower limits of nutrient amounts 144 (trace elements) and not exceeding upper limits for other nutrient amounts 144 (calories).

Continuing in reference to FIG. 1, alleviation program 152 may include a recommended nutrition plan and a recommended supplement plan that at least addresses viral biomarker 108, mitigates symptoms, side-effects, etc. Alleviation program 152 may contain a plan with timing of meals, calorie amounts, vitamin amounts, mineral amounts, etc. Alleviation program 152 may include food items combined with a supplement of non-food items. Alleviation program 152 may be presented as a function of reversing, treating, and/or preventing viral infection for non-infected individuals, for instance an otherwise healthy person to reduce their current risk during an outbreak.

Continuing in reference to FIG. 1, generating the viral alleviation program 152 may include generating a viral prevention metric, wherein the viral prevention metric reflects the level of user participation in the viral alleviation program 152. A "viral prevention metric," as used in this disclosure, is a numerical value, metric, parameter, and the like, described by a function, vector, matrix, or any other mathematical arrangement, which enumerates a user's current viral infection risk as a function of their level of participation in viral alleviation program 152. Viral prevention metric 160 may include using a machine-learning process, algorithm, and/or model to derive a numerical scale along which to provide a numerical value according to a user's viral epidemiological profile 112 and participation in alleviation program 152 generated from viral epidemiological profile 112. For instance, such a machine-learning model may be trained with training data, wherein training data contains data entries of nutrient amounts 144 correlated to viral infection prevention. Such a machine-learning model with said training data may be used by computing device 104 to relate the consumption of particular foods in alleviation program 152, to achieving some level of nutrient amount 144, and how the nutrient amount 144 relates to viral infection treatment and prevention, achieving remission, maintaining remission, etc. The current risk of infection may be enumerated in viral prevention metric 160. Such a viral prevention metric 160 may include a score that increases with participation in alleviation program 152 and/or decreases by falling short of nutrient amounts 144. Alleviation program 152 may include one or more treatment plans that incorporate, for instance and without limitation, large quantities of acai berry and other antioxidants, phytonutrients, and bioactive ingredients to prevent oxidative damage that leads to the presence of free radicals. Alleviation program 152 may be focused on mitigating tissue damage due to viral infection for an infected patient, where viral prevention metric 160 is tied to treatment, increasing with achieving full recovery, and again increasing with each timepoint a user remains uninfected.

Continuing in reference to FIG. 1, in non-limiting illustrating examples, falling short of vitamin E and vitamin K nutrient amounts 144, may have a particular effect on viral prevention metric 160 for an individual who has been classified to "skin viral infection" viral infection category 124. Where, chronically falling short of the nutrient amount 144 results in a (−3 score) each month but falling within the nutrient amount 144 range for those two nutrients affords (+1 score for each) every month; the target amount for the preceding month may dictate the score change for each subsequent month. In such a case, a machine-learning model may derive an algorithm which dictates the amount to increase/decrease viral prevention metric 160 for that particular viral infection category 124 according to the nutrient amounts 144. In this case, the machine-learning model is trained to identify the relationship between nutrient amounts 144 and effect on viral infection prevention to derive an equation that relates scoring criteria. The score is then calculated using the model and nutrition data as an input. "Nutrition data," as used in this disclosure, is data describing consumption by the user. Consumption by the user may include amounts and identities of nutrition elements 120. In this way, system 100 may calculate a viral prevention metric 160 as a function of a user's participation in alleviation program 152, where viral prevention metric 160 is updated with each nutrition element 120 consumed by user.

Continuing in reference to FIG. 1, generating the viral alleviation program 152 may include calculating a change in incidence of viral infection as a function of adhering to alleviation program 152. Calculating a change in incidence of viral infection may include receiving nutritional input from a user, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. Nutritional input of a user may include a designation of any nutrition elements 120 user may have consumed. Nutritional elements 120 may have nutrient amounts 144 associated therewith, which may be applied to a user's current viral epidemiological profile 112, viral infection category 124, and the like. Applying the nutrient amounts 144 may include calculating a difference in viral prevention metric 160. Applying the nutrient amounts 144 may include calculating a change in viral infection risk, likelihood, or incidence as a function of achieving nutrient amounts 144, as described above.

Continuing in reference to FIG. 1, generating the viral alleviation program 152 may include receiving a user preference regarding the plurality of nutrition elements 120, and modifying the plurality of nutrition elements 120 as a function of the user preference. A "user preference," as used in this disclosure, is a user input that designates a preference related to at least a nutrition element 120. User preference may include designations of nutrition elements 120 to avoid and/or include such as particular food groups, condiments, spices, dietary restrictions such as no animal products, cuisine type such as Mediterranean foods, time of day for eating such as fasting before 10 am, etc. In this way, computing device 104 may accept an input of user preference filter, sort, classify, or otherwise modify the data structure of nutrition elements 120 and schedule the nutrition elements 120 into alleviation program 152 in a custom, per-user manner. Computing device 104 may modify the plurality of nutrition elements 120 as a function of the user preference, for instance by providing recipes with steps omitted, new steps added, or entirely new recipes altogether utilizing the same or different nutrition elements 120. Computing device 104 may modify the plurality of nutrition elements 120 as a function of the user preference by generating a new file, based on the preference, and storing and/or retrieving the file from a database, as described in further detail below.

Figure 2:
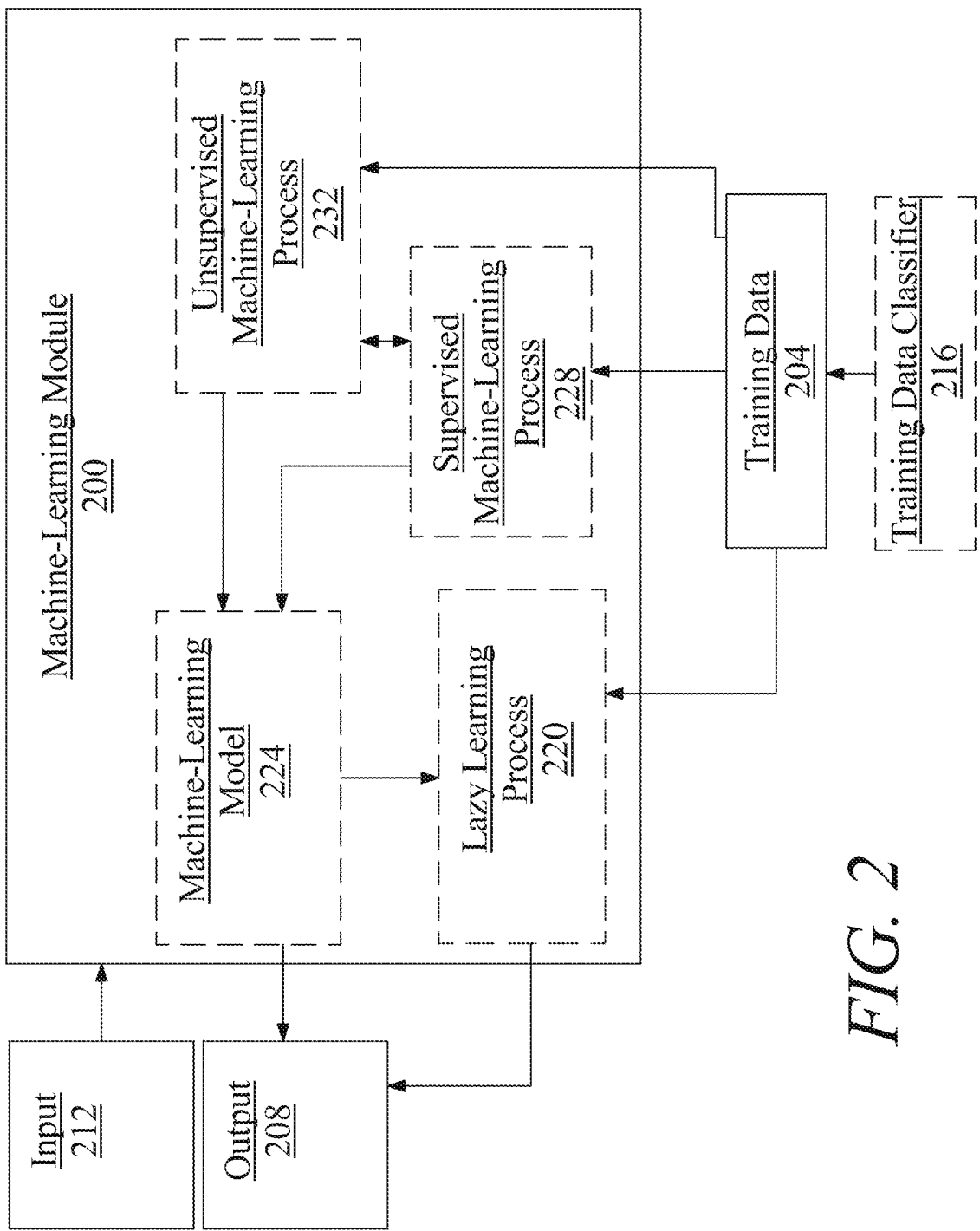
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of viral biomarkers 108 (such as gene expression patterns as it relates to viral epidemiological profile 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying nutrition elements 120 to viral infection category 124 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to viral epidemiological profile 112 and/or viral prevention metric 160, etc., as described above, to "learn" the upper and lower limits to the numerical scale, the increments to providing scoring, and the criteria for increasing and decreasing elements encompassed in the viral epidemiological profile 112 and/or viral prevention metric 160, etc. A machine-learning model may be used to "learn" which elements of viral biomarkers 108 have what effect on viral epidemiological profile 112, and which elements of viral epidemiological profile 112 are affected by particular nutrition elements 120 and the magnitude of effect, etc. The magnitude of the effect may be enumerated and provided as part of system 100, where nutrition elements 120 are communicated to user for their viral infection preventative properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a viral epidemiological profile 112 (potentially classified into viral infection categories 124), as described above as inputs, nutrient element 120 outputs, and a ranking function representing a desired form of relationship to be detected between inputs and outputs; ranking function may, for instance, seek to maximize the probability that a given input (such as nutrient amounts 144) and/or combination of inputs is associated with a given output (alleviation program 152 that incorporate nutrient elements 120 to achieve nutrient amounts 144 that are 'best' for viral infection category 124) to minimize the probability that a given input is not associated with a given output, for instance finding the most suitable times to consume meals, and what the meals should be, etc. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
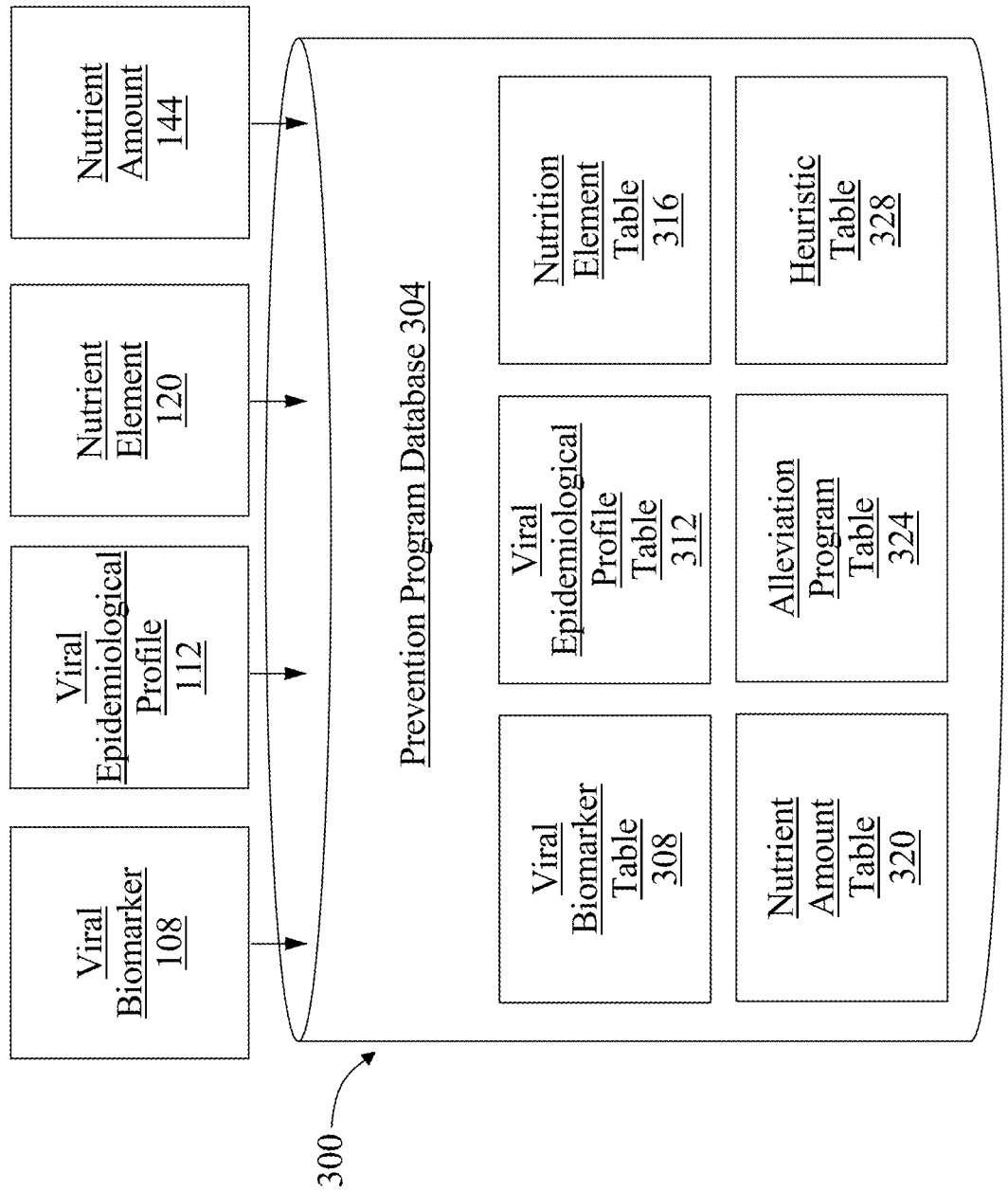
FIG. 3 is a block diagram of a alleviation program database.

Referring now to FIG. 3, a non-limiting exemplary embodiment 300 of a alleviation program database 304 is illustrated. Viral biomarker(s) 108 for a plurality of subjects, for instance for generating a training data classifier 216, may be stored and/or retrieved in alleviation program database 304. Viral biomarker 108 data from a plurality of subjects for generating training data 204 may also be stored and/or retrieved from a alleviation program database 304. Training data for spread model 140, such as a plurality of epidemiological factors, including data from municipal health authorities, viral incidence tracking, contact tracing data, and the like, may be stored and/or retrieved in alleviation program database 304. Computing device 104 may receive, store, and/or retrieve training data 204, wearable device data, physiological sensor data, biological extraction data, and the like, from alleviation program database 304. Computing device 104 may store and/or retrieve viral classifier 128, spread model 140, nutrition machine-learning model 148, among other determinations, I/O data, models, and the like, from alleviation program database 304.

Continuing in reference to FIG. 3, alleviation program database 304 may be implemented, without limitation, as a relational database, a key-value retrieval database such as a NOSQL database, or any other format or structure for use as a database that a person skilled in the art would recognize as suitable upon review of the entirety of this disclosure. Alleviation program database 304 may alternatively or additionally be implemented using a distributed data storage protocol and/or data structure, such as a distributed hash table and the like. Alleviation program database 304 may include a plurality of data entries and/or records, as described above. Data entries in a alleviation program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, alleviation program database 304 may include, without limitation, viral biomarker table 308, viral epidemiological profile table 312, nutrition element table 316, nutrient amount table 320, alleviation program table 324, and/or heuristic table 328. Determinations by a machine-learning process, machine-learning model, ranking function, and/or classifier, may also be stored and/or retrieved from the alleviation program database 304. As a non-limiting example, alleviation program database 304 may organize data according to one or more instruction tables. One or more alleviation program database 304 tables may be linked to one another by, for instance in a non-limiting example, common column values. For instance, a common column between two tables of alleviation program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a alleviation program database 304 may include, as a non-limiting example, a viral biomarker table 308, which may include categorized identifying data, as described above, including genetic data, epigenetic data, viral markers of infection, physiological data, biological extraction data, and the like. Viral biomarker table 308 may include viral biomarker 108 categories according to gene expression patterns, SNPs, mutations, cytokine concentrations, protein phosphorylation data, tissue stress data, data concerning metabolism of nutrition elements 120, such as user-specific pharmacokinetics, nutrient absorption, etc.; categories may include tables linked to mathematical expressions that describe the impact and/por relationship of each viral biomarker 108 datum on viral epidemiological profile 112, for instance threshold values for the cytokine expression biomarkers, etc., as it relates to viral infection, viral infection category 124, etc. One or more tables may include viral epidemiological profile table 312, which may include data regarding viral biomarker 108, thresholds, scores, metrics, values, categorizations, and the like, that system 100 may use to calculate, derive, filter, retrieve and/or store current viral infection levels, viral infection types, likelihood of currently having n infection, probability of future infection, nutritional deficiency, and the like. One or more tables may include nutrition element table 316, which may include data on nutrition elements 120 such as foods, ingredients, supplements, bioactive ingredients, phytonutrients, antioxidants, pharmaceuticals, and the like, for instance as classified to viral infection category 124, classified to data from alike subjects with similar viral biomarker(s) 108, as related to viral epidemiological profile 112, and the like, that system 100 may use to calculate, derive, filter, retrieve and/or store nutrition elements 120. One or more tables may include nutrient amount table 320, which may include functions, model, equations, algorithms, and the like, using to calculate or derive nutrient amounts 144 relating to viral epidemiological profile 112 and/or viral infection category 124, may include nutrient amounts 144 organized by nutrient, nutrient classification, user age, sex, viral infection severity, infection risk, climate, time of year, etc. One of more tables may include a alleviation program table 324, which may include nutrition element 120 identifiers, serving sizes, and/or timetables associated with nutrition elements 120, regarding times to eat, identifiers of meals, recipes, ingredients, schedules, diet types, and the like. One or more tables may include, without limitation, a heuristic table 328, which may organize rankings, scores (e.g. viral prevention metric) models (e.g. spread model 140), classifiers (e.g. viral classifier 128), outcomes, functions, numerical values, scales, arrays, matrices, and the like, that represent determinations, probabilities, metrics, parameters, values, and the like, include one or more inputs describing potential mathematical relationships, as described herein.

Referring now to FIGS. 4A and 4B, a non-limiting exemplary embodiment 400 of a viral epidemiological profile 112 is illustrated. Viral epidemiological profile 112 may include a variety of viral biomarker 108 categories, for instance 22 distinct categories, as shown in FIGS. 4A and 4B. each viral biomarker 108 may be assigned a value, such as an arbitrary value, where some viral biomarkers 108, such as those shaded in light grey, may relate to absolute scales from [0, x], where x is a maximal value and the range of values for the viral biomarker 108 cannot be below a 'zero amount'. Some viral biomarkers 108, such as those shaded in dark grey, may relate to cytokine levels, wherein, the viral biomarker 108 is enumerated as a 'box plot' that illustrates the range of expression in a population of users organized according to, for instance tissue type, normal vs infected state, etc.). In such an example, the dashed line may relate to a 'normal threshold' above which is elevated gene expression, below which is decreased expression level. Each viral biomarker 108 may have associated with it a numerical score, or some other identifying mathematical value that computing device 104 may assign. Persons skilled in the art may appreciate that for each user, any number of viral biomarkers 108 may be enumerated and assigned a value according to viral epidemiological profile machine-learning model 116. Viral epidemiological profile 112 may be graphed, or otherwise displayed, according to the enumeration by viral epidemiological profile machine-learning model 116. Each bar of the bar graph, or combinations of bar graph categories, may instruct a classification of a user's viral epidemiological profile 112 to a viral infection category 124.

Still referring now to FIGS. 4A and 4B, in non-limiting exemplary illustrations viral epidemiological profile 112 may be classified to a viral infection category 124. Some and/or all of the viral biomarkers 108 summarized in viral epidemiological profile 112 may be used to classify an individual to a particular viral infection category 124. For instance, as shown in FIG. 4B, ten of the 22 viral biomarker 108 categories may be used to classify viral epidemiological profile 112 to one or more viral infection categories 124. Viral epidemiological profile machine-learning model 116 may be trained to assign viral biomarker 108 to a viral infection category 124, wherein computing device 104 may know the identity of viral infection category 124 according to which viral infection category 124 has the most identifying data points. Alternatively or additionally, viral epidemiological profile 112 may include categorizations of epidemiological factors, as described above, enumerated according to viral epidemiological profile machine-learning model 116 assigned values. Such data categories may work to increase accuracy of viral infection category 124 by thorough consideration of viral outbreak factors.

Figure 5:
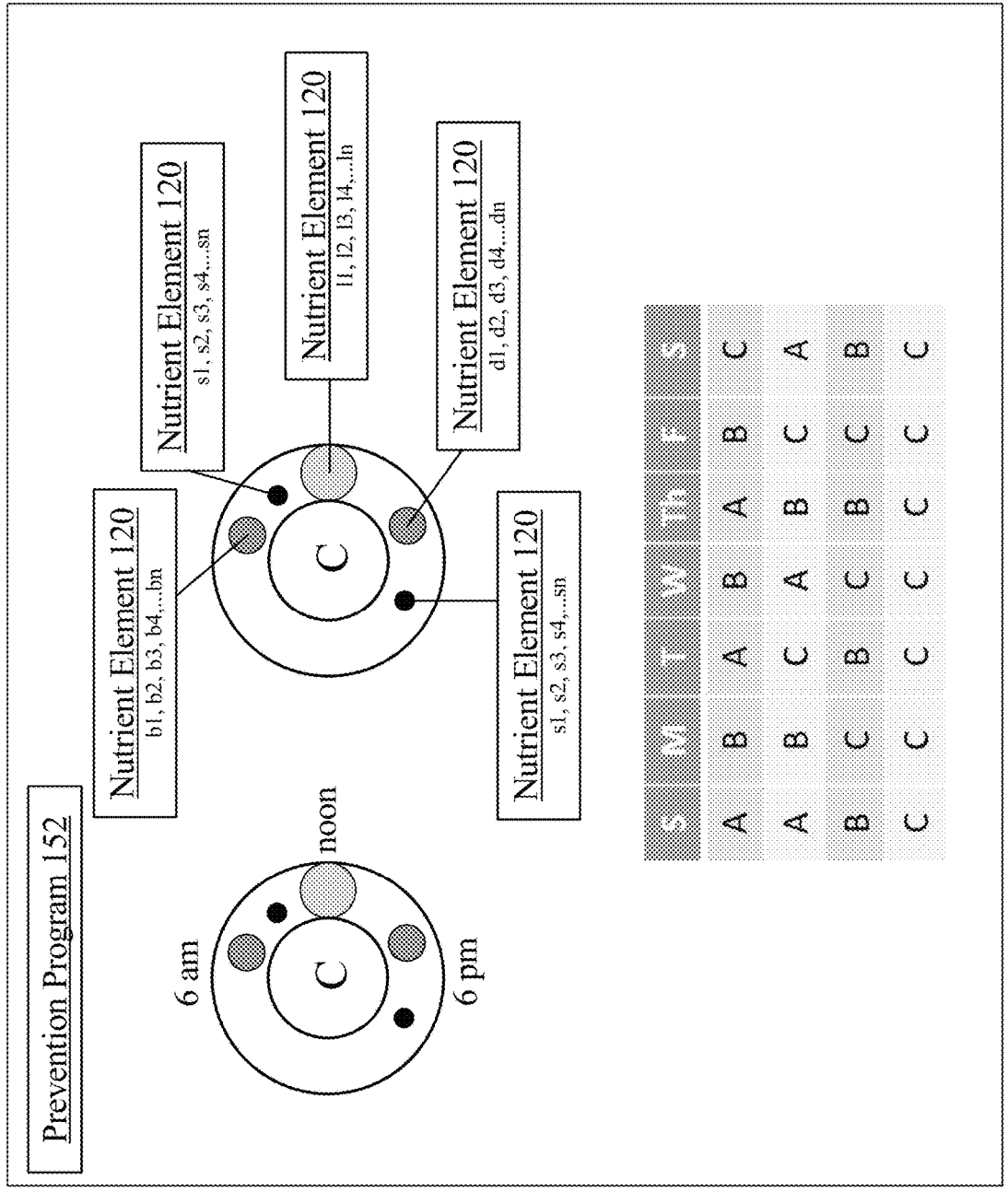
FIG. 5 is a diagrammatic representation of a viral alleviation program.

Referring now to FIG. 5, a non-limiting exemplary embodiment 500 of a viral alleviation program 152 is illustrated. Alleviation program 152 may include a schedule for arranging nutrition elements 120, according to for instance a 24-hour timetable, as designated on the left, where consumption is planned along a user's typical day-night cycle, beginning at ~6 am until just after 6 pm. Nutrition element 120 may include breakfast (denoted as mid-sized dark grey circle), which may correspond to a file of breakfast-related plurality of nutrition elements 120 (denoted b1, b2, b3, b4 . . . bn, to the nth breakfast item). Nutrition element 120 may include snacks eaten throughout the day to, for instance achieve nutrient amounts 144 missing from meals (denoted as small black circles), which may correspond to a file of snacking-related plurality of nutrition elements 120 (denoted s1, s2, s3, s4 . . . sn, to the nth snacking item). Nutrition element 120 may include dinner (denoted as large-sized light grey circle), which may correspond to a file of dinner-related plurality of nutrition elements 120 (denoted d1, d2, d3, d4 . . . dn, to the nth dinner item). Alleviation program 152 may include a variety of diets, as denoted in the monthly schedule at the bottom, Sunday through Saturday. Alleviation program 152 'C' is shown, which may be an idealistic goal for user to achieve by the end of the month, where alleviation program 'A' and 'B' are intermediate plans intended to wean user to the 'ideal' plan. Nutrition elements 120 classified by 'meal type' may be further modified by 'A' and 'B' according to user preferences 148 collected by computing device 104 throughout the process. Circle sizes, denoting nutrition element 120 classes may relate to portion sizes, which are graphed along the circle corresponding to the times they are expected to be consumed. User may select which nutrition element 120 from each category is to be consumed, and when it was consumed, to arrive at viral prevention metric 160; this is to say viral prevention metric 160 may be iteratively updated as a function of the user-selected nutrition element 120 output from system 100.

Figure 6:
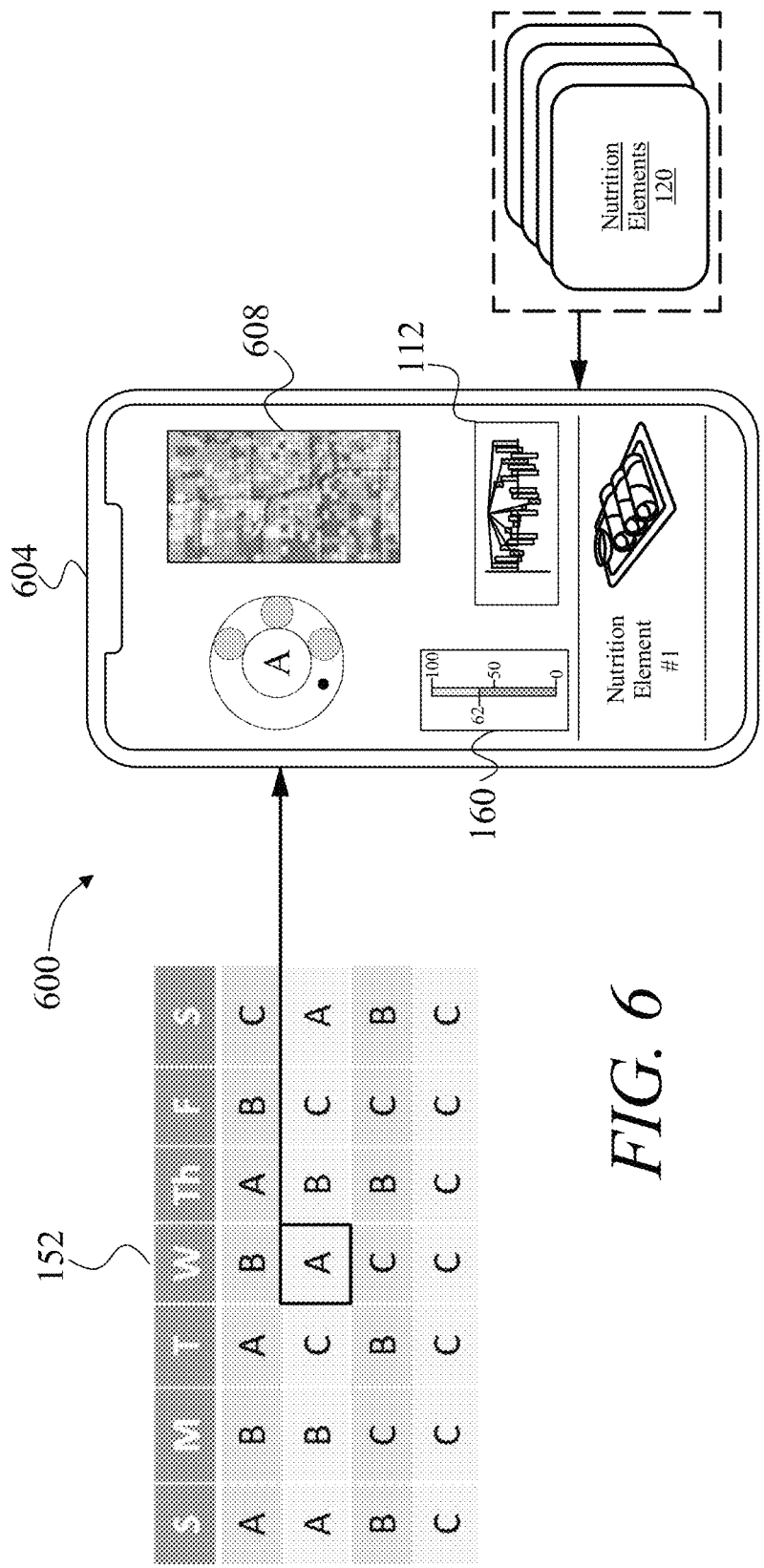
FIG. 6 is a diagrammatic representation of a user device.

Referring now to FIG. 6, a non-limiting exemplary embodiment 600 of a user device 604 is illustrated. User device 604 may include computing device 104, a "smartphone," cellular mobile phone, desktop computer, laptop, tablet computer, internet-of-things (JOT) device, wearable device, among other devices. User device 604 may include any device that is capable for communicating with computing device 104, alleviation program database 304, or able to receive, transmit, and/or display, via a graphical user interface, viral epidemiological profile 112, nutrition element 120, alleviation program 152, viral prevention metric 160, among other outputs from system 100. User device 604 may provide a viral epidemiological profile 112, for instance as a collection of metrics determined from viral biomarker 108 data. User device 604 may provide viral infection category 124 that was determined as a function of parameters/determinations enumerated in viral epidemiological profile 112. User device 604 may provide data concerning nutrient amounts 144, including the levels of specific nutrients, nutrient ranges, nutrients to avoid, etc. User device 604 may link timing of foods to preemptive ordering interface for ordering a nutrition element 120, for instance and without limitation, through a designated mobile application, mapping tool or application, etc., and a radial search method about a user's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display nutrient elements 120 as a function of location, for instance and without limitation, as described in User device 604 may link nourishment consumption program 120 to a scheduling application, such as a 'calendar' feature on user device, which may set audio-visual notifications, timers, alarms, and the like. May select locations for nutrition elements 120 based on entity affinity to viral infection research, viral infection charity, etc.

Continuing in reference to FIG. 6, user device 604 may provide viral epidemiology map 608. "Viral epidemiology map," as used in this disclosure, is a graphical display of viral epidemiology factors as summarized in viral epidemiology profile 112. Viral epidemiology map 608 may include a heat map, or coloring scale of geographical regions on a map as a function of viral risk, viral case numbers, etc. Viral epidemiology map 608 may include any graphical, text-based, icon-based, or the like, display of geographic information software (GIS) meant to convey the phylogenetics and epidemiology of a virus in a human population as generated from spread model 140 using viral spread training data 136. Viral epidemiology map 608 map include applying spread model 140 outputs to a geographical mapping about the user, for instance using the Internet and a mapping tool, algorithm, or mapping application (e.g. GOOGLE MAPS), or the like. User device 604 may determine a user's current location and apply the outputs of spread model 140 to illustrate the current viral epidemiological landscape. User device 604 may update viral infection profile 112 as a function of the viral epidemiology map 608. User device 604 may update viral prevention metric 160 as a function of user participation in alleviation program 152, as indicated from selected nutrition elements 120.

Figure 7:
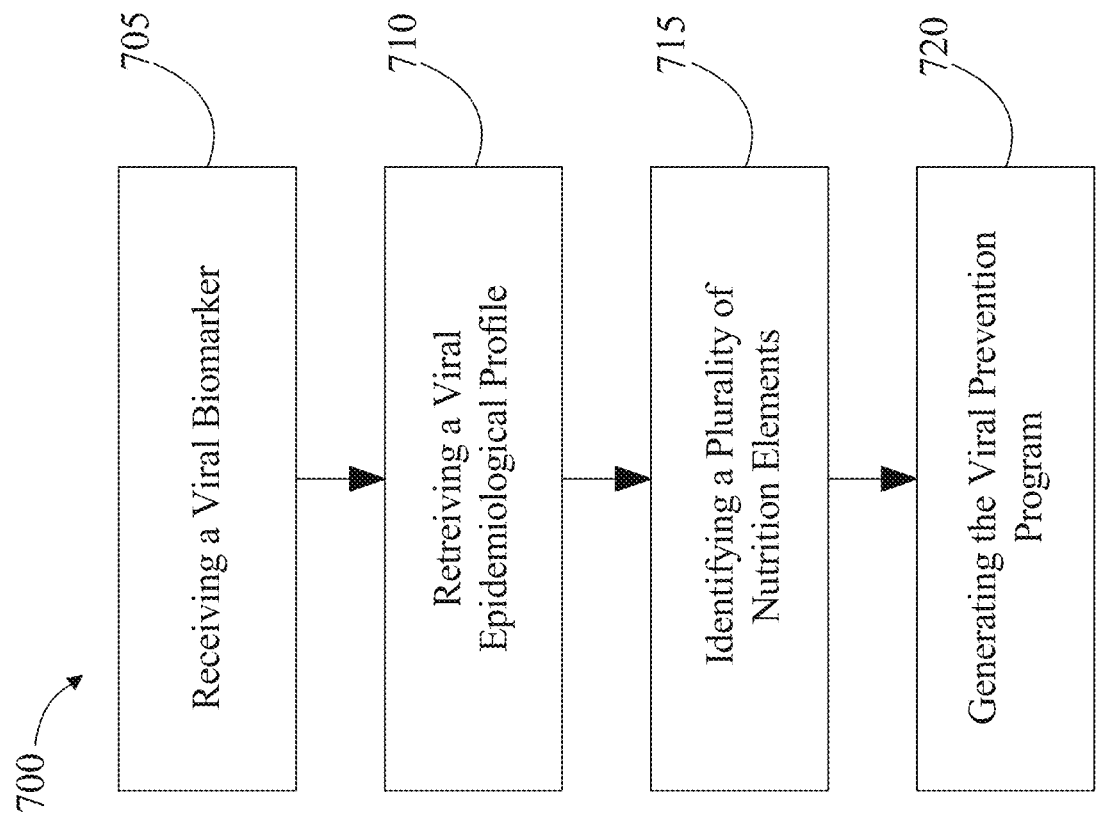
FIG. 7 is a block diagram of a workflow of a method for generating a viral alleviation program.

Referring now to FIG. 7, an exemplary embodiment 700 of a method for generating a viral alleviation program is illustrated. At step 705, the method including receiving, by a computing device 104, at least a viral biomarker 108 relating to a user. Receiving at least a viral biomarker 108 may include receiving a result of one or more tests relating the user; this may be implemented, without limitation, as described above in FIGS. 1-6.

Still referring to FIG. 7, at step 710, method includes retrieving, by the computing device 104, a viral epidemiological profile 112 related to the user. of a plurality of epidemiological factors as a function of at least a viral biomarker 108. Retrieving the viral epidemiological profile 112 may include receiving viral epidemiological profile 112 training data, training a viral epidemiological profile machine-learning model 116 with training data that includes a plurality of data entries wherein each entry correlates viral biomarkers 108 to a plurality of epidemiological factors, and generating the viral epidemiological profile 112 as a function of the viral epidemiological profile machine-learning model 116 and at least a viral biomarker 108; this may be implemented, without limitation, as described above in FIGS. 1-6.

Continuing in reference to FIG. 7, at step 715, method includes identifying, by the computing device 104 and using the viral epidemiological profile 112, a plurality of nutrition elements 120 for the user, wherein identifying includes assigning the viral epidemiological profile 112 to a viral infection category 124, wherein the viral infection category 124 is a determination about a current viral epidemiological state of the user, calculating, according to the viral infection category 124, a plurality of nutrient amounts 144, wherein calculating a plurality of nutrient amounts 144 includes determining an effect of the plurality of nutrient amounts 144 on the viral epidemiological profile 112, and calculating the plurality of nutrient amounts 144 as a function of the effect, wherein the plurality of nutrient amounts 144 is a plurality of amounts intended to result in prevention of viral infection. Identifying, as a function of the plurality of nutrient amounts 144, the plurality of nutrition elements 120, wherein the plurality of nutrition elements 132 are intended to prevent viral infection as a function of the viral infection category 124. Assigning the viral epidemiological profile 112 to a viral infection category 124 may include training a viral classifier 128 using a viral classification machine-learning process 132 and training data which includes a plurality of data entries wherein each data entry correlates viral biomarkers 108 to a viral infection category 124 and assigning the viral infection category 124 as a function of the viral classifier and the viral epidemiological profile 112. Determining the effect of the plurality of nutrient amounts 144 on the viral epidemiological profile 112 may include receiving viral spread training data 136, generating a spread model 140, wherein the spread model 140 is a machine-learning model trained with the viral spread training data 136 which includes a plurality of data entries that models a plurality of effects of the plurality of nutrient amounts 144 on viral spread rates, and determining the effect of the plurality of nutrient amounts 144 as a function of the spread model 140. Calculating the plurality of nutrient amounts 144 may include determining the plurality of nutrient amounts 144 as a function of at least a viral biomarker 108 and the plurality of effects. Calculating nutrient amounts 144 may include generating training data using the plurality of effects of the plurality of nutrient amounts 144 identified according to the viral infection category 124, training a nutrition machine-learning model 148 according to the training data, wherein training data includes a plurality of data entries that correlates the magnitude of nutrient effect to a plurality of nutrient amounts for each viral infection category 124, and calculating nutrient amounts 144 as a function of the nutrition machine learning model 148 and the viral infection category 124; this may be implemented, without limitation, as described above in FIGS. 1-6.

Continuing in reference to FIG. 7, at step 720, method includes generating, by the computing device 104, using the plurality of nutrition elements 120, the viral alleviation program 152. Generating viral alleviation program 152 may include generating a alleviation program classifier 156 using a nourishment classification machine-learning process to classify the plurality of nutrient amounts 144 to the plurality of nutrition elements 120 and outputting the plurality of nutrition elements 120 as a function of the alleviation program classifier 156. Generating viral alleviation program 152 may include generating a viral prevention metric 160, wherein the viral prevention metric 160 reflects the level of user participation in viral alleviation program 152. Generating viral alleviation program 152 may include calculating a change in incidence of viral infection as a function of adhering to alleviation program 152; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding may readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
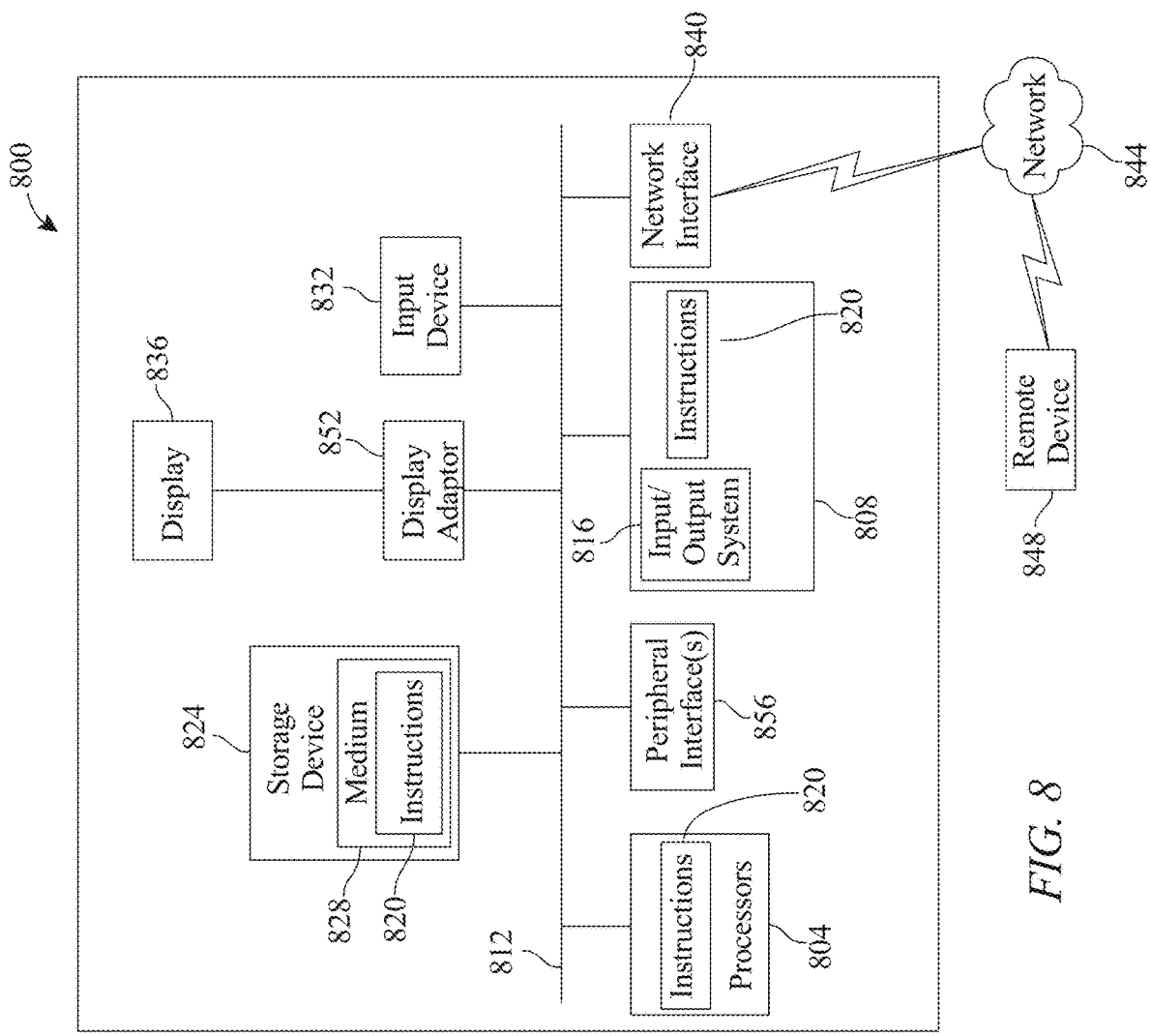
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions may be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a viral alleviation program, the system comprising a computing device, wherein the computing device is configured to:
   receive at least a viral biomarker relating to a user;
   retrieve a viral epidemiological profile related to the user;
   identify, using the viral epidemiological profile, a plurality of nutrition elements for the user, wherein identifying comprises:
      assigning the viral epidemiological profile to a viral infection category;
      calculating, according to the viral infection category, a plurality of nutrient amounts, wherein calculating a plurality of nutrient amounts includes:
         determining an effect of the plurality of nutrient amounts on the viral epidemiological profile, wherein the determining comprises:
            receiving viral spread training data including a plurality of data entries, wherein each data entry of the plurality of data entries indicates links between the at least a nutrient amount to viral spread rates in a region;
            training a spread machine-learning model as a function of the viral spread training data; and
            determining the effect of the plurality of nutrient amounts as a function of the spread machine-learning model; and
         calculating the plurality of nutrient amounts as a function of the effect;
      identifying, as a function of the plurality of nutrient amounts and the viral infection category, the plurality of nutrition elements; and
   generate, using the plurality of nutrition elements, viral alleviation program.

2. The system of claim 1, wherein receiving the at least a viral biomarker further comprises receiving a result of at least a test relating to the user.

3. The system of claim 1, wherein retrieving the viral epidemiological profile further comprises:
   receiving viral epidemiological profile training data including a plurality of data entries wherein each data entry of the plurality of data entries correlates viral incidence data with a plurality of epidemiological factors;
   training a viral epidemiological profile machine-learning model as a function of the viral epidemiological profile training data; and
   generating the viral epidemiological profile as a function of the viral epidemiological profile machine-learning model and the at least a viral biomarker.

4. The system of claim 1, wherein assigning the viral epidemiological profile to the viral infection category further comprises:
   training a viral classifier using a viral classification machine-learning process and training data, wherein the training data includes a plurality of data entries, each correlating viral biomarkers to a viral infection category; and
   assigning the viral infection category as a function of the viral classifier and the viral epidemiological profile.

5. The system of claim 1, wherein calculating the plurality of nutrient amounts further comprises calculating the plurality of nutrient amounts as a function of the at least a viral biomarker and the plurality of effects.

6. The system of claim 5, wherein calculating nutrient amounts further comprises:
   generating training data using the plurality of effects, wherein training data includes a plurality of data entries that correlates the magnitude of effect to a plurality of nutrient amounts for each viral infection category;
   training a nutrition machine-learning model according to the training data; and
   calculating nutrient amounts as a function of the nutrition machine learning model and the viral infection category.

7. The system of claim 1, wherein generating viral alleviation program further comprises:
   generating a alleviation program classifier using a nourishment classification machine-learning process; and
   outputting the plurality of nutrition elements as a function of the alleviation program classifier.

8. The system of claim 1, wherein generating viral alleviation program further comprises generating a viral prevention metric, wherein the viral prevention metric reflects the level of user participation in viral alleviation program.

9. The system of claim 1, wherein generating viral alleviation program further comprises calculating a change in incidence of viral infection as a function of adhering to alleviation program.

10. A method for generating a viral alleviation program, the method comprising:
    receiving, by a computing device, at least a viral biomarker relating to a user;
    retrieving, by the computing device, a viral epidemiological profile related to the user;
    identifying, by the computing device, using the viral epidemiological profile, a plurality of nutrition elements for the user, wherein identifying comprises:
      assigning the viral epidemiological profile to a viral infection category;
      calculating, according to the viral infection category, a plurality of nutrient amounts, wherein calculating a plurality of nutrient amounts includes:
        determining an effect of the plurality of nutrient amounts on the viral epidemiological profile, wherein the determining comprises:
          receiving viral spread training data including a plurality of data entries, wherein each data entry of the plurality of data entries indicates links between the at least a nutrient amount to viral spread rates in a region;
          training a spread machine-learning model as a function of the viral spread training data; and
          determining the effect of the plurality of nutrient amounts as a function of the spread model; and
        calculating the plurality of nutrient amounts as a function of the effect;
      identifying, as a function of the plurality of nutrient amounts and the viral infection category, the plurality of nutrition elements; and
    generating, by the computing, using the plurality of nutrition elements, viral alleviation program.

11. The method of claim 10, wherein receiving the at least a viral biomarker further comprises receiving a result of at least a test relating to the user.

12. The method of claim 10, wherein retrieving the viral epidemiological profile further comprises:
    receiving viral epidemiological profile training data including a plurality of data entries wherein each data entry of the plurality of data entries correlates viral incidence data with a plurality of epidemiological factors;
    training a viral epidemiological profile machine-learning model as a function of the viral epidemiological profile training data; and
    generating the viral epidemiological profile as a function of the viral epidemiological profile machine-learning model and the at least a viral biomarker.

13. The method of claim 10, wherein assigning the viral epidemiological profile to the viral infection category further comprises:
    training a viral classifier using a viral classification machine-learning process and training data, wherein the training data includes a plurality of data entries, each correlating viral biomarkers to a viral infection category; and
    assigning the viral infection category as a function of the viral classifier and the viral epidemiological profile.

14. The method of claim 10, wherein calculating the plurality of nutrient amounts further comprises calculating the plurality of nutrient amounts as a function of the at least a viral biomarker and the plurality of effects.

15. The method of claim 14, wherein calculating nutrient amounts further comprises:
    generating training data using the plurality of effects, wherein training data includes a plurality of data entries that correlates the magnitude of effect to a plurality of nutrient amounts for each viral infection category;
    training a nutrition machine-learning model according to the training data; and
    calculating nutrient amounts as a function of the nutrition machine learning model and the viral infection category.

16. The method of claim 10, wherein generating viral alleviation program further comprises:
    generating a alleviation program classifier using a nourishment classification machine-learning process; and outputting the plurality of nutrition elements as a function of the alleviation program classifier.

17. The method of claim 10, wherein generating viral alleviation program further comprises generating a viral prevention metric, wherein the viral prevention metric reflects the level of user participation in viral alleviation program.

18. The method of claim 10, wherein generating viral alleviation program further comprises calculating a change in incidence of viral infection as a function of adhering to alleviation program.

* * * * *